United States Patent
Reddy et al.

(10) Patent No.: US 11,492,669 B2
(45) Date of Patent: *Nov. 8, 2022

(54) MICRORNA-455-3P AS A PERIPHERAL BIOMARKER FOR ALZHEIMER'S DISEASE

(71) Applicant: Texas Tech University System, Lubbock, TX (US)

(72) Inventors: P. Hemachandra Reddy, Lubbock, TX (US); Subodh Kumar, Lubbock, TX (US)

(73) Assignee: Texas Tech University System, Lubbock, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/630,068

(22) PCT Filed: Jul. 12, 2018

(86) PCT No.: PCT/US2018/041840
§ 371 (c)(1),
(2) Date: Jan. 10, 2020

(87) PCT Pub. No.: WO2019/014457
PCT Pub. Date: Jan. 17, 2019

(65) Prior Publication Data
US 2020/0354790 A1    Nov. 12, 2020

Related U.S. Application Data

(60) Provisional application No. 62/531,760, filed on Jul. 12, 2017.

(51) Int. Cl.
*C12Q 1/6883* (2018.01)
*A61K 31/7088* (2006.01)

(52) U.S. Cl.
CPC ........ *C12Q 1/6883* (2013.01); *A61K 31/7088* (2013.01); *C12Q 2600/158* (2013.01); *C12Q 2600/178* (2013.01); *G01N 2800/2821* (2013.01); *G01N 2800/60* (2013.01)

(58) Field of Classification Search
CPC .... C12Q 1/68; C12Q 1/686; C12Q 2600/178; C12Q 2600/158; C12Q 2600/118; C12Q 2600/112; C12Q 2545/114
See application file for complete search history.

(56) References Cited

U.S. PATENT DOCUMENTS

| | | | |
|---|---|---|---|
| 9,188,595 B2 | 11/2015 | Zhao et al. | |
| 2012/0088816 A1 | 4/2012 | Zama et al. | |
| 2013/0040303 A1* | 2/2013 | Wang | G16B 20/00 435/6.12 |
| 2014/0031245 A1 | 1/2014 | Khan et al. | |
| 2014/0302068 A1 | 10/2014 | Khoo et al. | |
| 2014/0303025 A1* | 10/2014 | Van Keuren-Jensen | C12Q 1/6883 506/9 |
| 2014/0378439 A1 | 12/2014 | Dezso et al. | |
| 2020/0190588 A1* | 6/2020 | Moller | C12Q 1/6883 |

FOREIGN PATENT DOCUMENTS

| | | | |
|---|---|---|---|
| CN | 104774929 A | 7/2015 | |
| KR | 1020170127089 | 11/2017 | |
| WO | 2009009457 A1 | 1/2009 | |
| WO | WO-2012145363 A1 * | 10/2012 | ........... C12Q 1/6883 |
| WO | 2013003350 A2 | 1/2013 | |
| WO | WO-2015179909 A1 * | 12/2015 | ........... C12Q 1/6883 |

OTHER PUBLICATIONS

Noble et al., Protein kinase inhibitors: insights into drug design from structure, Science, vol. 303, pp. 1800-1805. (Year: 2004).*
Kumar et al., A new discovery of microRNA-455-3p in Alzheimer's disease, Journal of Alzheimer's disease, vol. 72, pp. S117-S130. (Year: 2019).*
Alexandrov PN, et al. (2012) microRNA (miRNA) speciation in Alzheimer's disease (AD) cerebrospinal fluid (CSF) and extracellular fluid (ECF). Int J Biochem Mol Biol 3(4)365-373.
Adlakha YK, Saini N (2014) Brain microRNAs and insights into biological functions and therapeutic potential of brain enriched miRNA-128. Mol Cancer 13:33.
Alhasan AH, et al. (2016) Circulating microRNA signature for the diagnosis of very high-risk prostate cancer. Proc Natl Acad Sci U S A 113(38):10655-10660.
Bartel DP (2007) MicroRNAs: Genomics, Biogenesis, Mechanism and Function. Cell 116(2):281-297.
Boon RA, Vickers KC (2007) Intercellular Transport of MicroRNAs. Arterioscler Thromb Vasc Biol 33(2)186-192.
Burton, T. et al. (2002). Transforming growth factor-beta-induced transcription of the Alzheimer beta-amyloid precursor protein gene involves interaction between the CTCFcomplex and Smads. Biochem. Biophys. Res. Commun. 295, 713-723.

(Continued)

*Primary Examiner* — Dana H Shin
(74) *Attorney, Agent, or Firm* — Edwin S. Flores; Daniel J. Chalker; Chalker Flores, LLP

(57) ABSTRACT

The present invention includes a method for identifying an Alzheimer's disease (AD) patient prior to reaching clinical disease classification, comprising: obtaining a dataset associated with a blood, serum, or plasma sample from the patient, wherein the dataset comprises data representing the level of one or more microRNA biomarkers in the blood, serum, or plasma sample; assessing the dataset for a presence or an increase in an amount of miRNA-455-3p; determining the likelihood that the patient will develop AD patient prior to reaching clinical disease classification by detecting the presence or the increase in miRNA-455-3p to produce a score that is indicative of a likelihood of developing AD, wherein a higher score relative to a healthy control indicates that the patient is likely to have the prognosis for transitioning to classified AD, wherein the healthy control is derived from a non-AD patient with no clinical evidence of AD.

4 Claims, 10 Drawing Sheets

Specification includes a Sequence Listing.

(56) References Cited

OTHER PUBLICATIONS

Chen W, et al. (2016) MicroRNA-455-3p modulates cartilage development and degeneration through modification of histone H3 acetylation. Biochim Biophys Acta 1863(12):2881-2891.
Cheng JS, et al. (2009) Collagen VI protects neurons against Abeta toxicity. Nat Neurosci 12(2):119-121.
Cheng L, et al. (2015) Prognostic serum miRNA biomarker associated with Alzheimer's disease shows concordance with neuropsychological and neuroimaging assessment. Mol Psychiatry 20 (10):1188-1196.
Cheng, C. M. et al. (2016). Upregulation of miR-455-5p by the TGF-b-SMAD signalling axis promotes the proliferation of oral squamous cancer cells by targeting UBE2B. J. Pathol. 240, 38-49.
Das P, Golde T (2006) Dysfunction of TGF-beta signaling in Alzheimer's disease. J Clin Invest 116(11):2855-2857.
De Rossi, P. et al. (2016). Predominant expression of Alzheimer's disease associated BIN1 in mature oligodendrocytes and localization to white matter tracts. Mol. Neurodegener. 11:59.
DeKosky, S. T. et al. (1996). Structural correlates of cognition in dementia: quantification and assessment of synapse change. Neurodegeneration 5, 417-421.
Delay, C. et al., "MicroRNAs targeting Nicastrin regulate Aβ production and are affected by target site polymorphisms", Frontiers in Molecular Neuroscience, 2014, vol. 7, Article 67, pp. 1-7.
Dong H, et al. (2015) Serum microRNA profiles serve as novel biomarkers for the diagnosis of Alzheimer's disease. Dis. Markers (2015):625659.
Donovan LE, et al. (2013) Exploring the potential of the platelet membrane proteome as a source of peripheral biomarkers for Alzheimer's disease. Alzheimers Res Ther 5(3):32.
Du, H. et al. (2010). Early deficits in synaptic mitochondria in an Alzheimer's disease mouse model. Proc. Natl. Acad. Sci. U.S.A. 107, 18670-18675.
Ferguson, S. A., Panos, J. J., Sloper, D., and Varma, V. (2017). Neurodegenerative markers are increased in postmortemBA21 tissue fromAfrican Americans with Alzheimer's disease. J. Alzheimers Dis. 59, 57-66.
Ferrer I, et al. (2000) N-myc and c-myc expression in Alzheimer disease, Huntington disease and Parkinson disease. Brain Res Mol Brain Res. 77(2):270-276.
Freischmidt A, et al. (2014) Serum microRNAs in patients with genetic amyotrophic lateral sclerosis and pre-manifest mutation carriers. Brain 137(Pt 11):2938-2950.
Geekiyanage H, et al. (2012) Blood serum miRNA: Non-invasive biomarkers for Alzheimer's disease. Exp Neurol 235 (2):491-496.
Godfrey AC, et al. (2013) Serum microRNA expression as an early marker for breast cancer risk in prospectively collected samples from the Sister Study cohort. Breast Cancer Res 15(3):R42.
Ha M, Kim VN (2015) Regulation of microRNA biogenesis. Nat Rev Mol Cell Biol 15(8):509-524.
Hamam, R., Ali, A. M., Alsaleh, K. A., Kassem, M., Alfayez, M., Aldahmash, A., et al. (2016). microRNA expression profiling on individual breast cancer patients identifies novel panel of circulating microRNA for early detection. Sci. Rep. 6:25997.
Hsiao K, et al. (1996) Correlative memory deficits, Abeta elevation, and amyloid plaques in transgenic mice. Science 274(5284):99-102.
Jung, E. S. et al. (2015). Acute ER stress regulates amyloid precursor protein processing through ubiquitin-dependent degradation. Sci. Rep. 5:8805.
Jung, E. S. et al. (2016). p53-dependent SIRT6 expression protects Ab42-induced DNA damage. Sci. Rep. 6:25628.
Khan, T. K. et al. (2016). An internally controlled peripheral biomarker for Alzheimer's disease: Erk1 and Erk2 responses to the inflammatory signal bradykinin. Proc. Natl. Acad. Sci. U.S.A. 103, 13203-13207.
Knyazev EN, et al. (2016) MicroRNA hsa-miR-4674 in Hemolysis-Free Blood Plasma Is Associated with Distant Metastases of Prostatic Cancer. Bull Exp Biol Med 161(1):112-115.
Kumar P, et al. (2013) Circulating miRNA biomarkers for Alzheimer's disease. Plos One 8(7):e69807.

Kumar S, et al. (2014) Severity of hepatitis C virus (genotype-3) infection positively correlates with circulating microRNA-122 in patients sera. Dis Markers (2014):435476.
Kumar, S et al. (2016) Are circulating microRNAs peripheral biomarkers for Alzheimer's disease? Biochim Biophys Acta 1862(9):1617-1627.
Kumar, S. et al. (2017). MicroRNA-455-3p as a potential peripheral biomarker for Alzheimer's disease. Hum. Mol. Genet. 26, 3808-3822.
Kumar, S. et al., "MicroRNA-455-3p as a Potential Biomarker for Alzheimer's Disease: An Update", Frontiers in Aging Neuroscience, Feb. 23, 2018, vol. 10, Article 41, pp. 1-11.
Kuruva, C. S. et al. (2017). Aqua-soluble DDQ reduces the levels of Drp1 and Ab and inhibits abnormal interactions between Ab and Drp1 and protects Alzheimer's disease neurons from Ab- and Drp1-induced mitochondrial and synaptic toxicities. Hum. Mol. Genet. 26, 3375-3395.
LaFerla FM, et al. (2007) Intracellular amyloid-β in Alzheimer's disease. Nat Rev Neuro 8(7):449-509.
Lalevee S, et al. (2014) miR455 is linked to hypoxia signaling and is deregulated in preeclampsia. Cell Death Dis 5: e1408.
Lau, P. et al., "Alteration of the microRNA network during the progression of Alzheimer's disease", EMBO Molecular Medicine, 2013, vol. 5, pp. 1613-1634.
Lee HG, et al. (2006) Ectopic expression of phospho-Smad2 in Alzheimer's disease: uncoupling of the transforming growth factor-beta pathway?. J Neurosci Res 84(8):1856-1861.
Lee HG, et al. (2009) The neuronal expression of MYC causes a neurodegenerative phenotype in a novel transgenic mouse. Am J Pathol 174(3):891-897.
Li, Q. et al. (2004). TP73 allelic expression in human brain and allele frequencies in Alzheimer's disease. BMC Med. Genet. 5:14.
Li, Y. J. et al. (2016). MicroRNA-455 suppresses non-small cell lung cancer through targeting ZEB1. Cell Biol. Int. 40, 621-628.
Liu CC, et al. (2013) Apolipoprotein E and Alzheimer disease: risk, mechanisms and therapy. Nat Rev Neurol 9 (2):106-118.
Liu, J. et al. (2016). MiR-455-5p acts as a novel tumor suppressor in gastric cancer by down-regulating RAB18. Gene 592, 308-315.
Livak KJ, Schmittgen TD (2001) Analysis of relative gene expression data using real-time quantitative PCR and the 2-ΔΔCT method. Methods 25(4):402-408.
Lugli G, et al. (2015) Plasma Exosomal miRNAs in Persons with and without Alzheimer Disease: Altered Expression and Prospects for Biomarkers. PLoS One10(10):e0139233.
Lukiw J (2013) Circular RNA (circRNA) in Alzheimer's Disease (AD). Frontiers in Genetics 4:307.
Malkki, H. (2015). Alzheimer disease: NGF gene therapy activates neurons in the AD patient brain. Nat. Rev. Neurol. 11:548.
Manczak M, et al. (2016) Protective effects of reduced dynamin-related protein 1 against amyloid beta-induced mitochondrial dysfunction and synaptic damage in Alzheimer's disease. Hum Mol Genet 25(22):4881-4897.
Mastroeni D, et al. (2013) Reduced RAN expression and disrupted transport between cytoplasm and nucleus; a key event in Alzheimer's disease pathophysiology. PLoS One 8(1):e53349.
Mattson MP (2004) Pathways towards and away from Alzheimer's disease. Nature 430(7000):631-639.
Nunomura, A. et al. (2001). Oxidative damage is the earliest event in Alzheimer disease. J. Neuropathol. Exp. Neurol. 60, 759-767.
Qin, L., Zhang, Y., Lin, J., Shentu, Y., and Xie, X. (2016). MicroRNA-455 regulates migration and invasion of human hepatocellular carcinoma by targeting Runx2. Oncol. Rep. 36, 3325-3332.
Reddy PH, et al. (2010) Amyloid-β and mitochondria in aging and Alzheimer's disease: Implications for synaptic damage and cognitive decline. J Alz Dis 20(2010):S499-S512.
Reddy PH, et al. (2017) A critical evaluation of neuroprotective and neurodegenerative MicroRNAs in Alzheimer's disease. Biochem Biophys Res Commun 483(4):1156-1165.
Reddy, P. H. (2006). Amyloid precursor protein-mediated free radicals and oxidative damage: implications for the development and progression of Alzheimer's disease. J. Neurochem. 96, 1-13.

(56) References Cited

OTHER PUBLICATIONS

Reddy, P. H., and Beal,M. F. (2008). Amyloid beta, mitochondrial dysfunction and synaptic damage: implications for cognitive decline in aging and Alzheimer's disease. Trends Mol. Med. 14, 45-53.

Reddy, P. H., Manczak, M., Mao, P., Calkins, M. J., Reddy, A. P., and Shirendeb, U. (2010). Amyloid-beta and mitochondria in aging and Alzheimer's disease: implications for synaptic damage and cognitive decline. J. Alzheimers Dis. 20, S499-S512.

Reddy, P. H., Tonk, S., Kumar, S., Vijayan, M., Kandimalla, R., Kuruva, C. S., et al. (2017). A critical evaluation of neuroprotective and neurodegenerative MicroRNAs in Alzheimer's disease. Biochem. Biophys. Res. Commun. 483, 1156-1165.

Reddy, P. H., Tripathi, R., Troung, Q., Tirumala, K., Reddy, T. P., Anekonda, V., et al. (2012). Abnormal mitochondrial dynamics and synaptic degeneration as early events in Alzheimer's disease: implications to mitochondria targeted antioxidant therapeutics Biochim. Biophys. Acta 1822, 639-649.

Rosenmann H, et al. (2004) An association study of a polymorphism in the heparin sulfate proteoglycan gene (perlecan, HSPG2) and Alzheimer's disease. Am J Med Genet B Neuropsychiatr Genet 128B(1):123-125.

Satoh J, Kino Y, Niida S (2015) MicroRNA-Seq data analysis pipeline to identify blood biomarkers for Alzheimer's disease from public data. Biomarker Insights 10:21-31.

Schipper HM, et al. (2007) microRNA expression in Alzheimer blood mononuclear cells. Gene Regul Syst Biol 20 (1):263-274.

Shackleton, B., Crawford, F., and Bachmeier, C. (2017). Apolipoprotein E mediated modulation of ADAM10 in Alzheimer's disease. Curr. Alzheimer Res. 14, 578-585.

Shi WL, et al. (2016) Integrated miRNA and mRNA expression profiling in fetal hippocampus with Downsyndrome. J Biomed Sci 23(1):48.

Sindi, I. A. et al. (2014). Role for the neurexinneuroligin complex in Alzheimer's disease. Neurobiol. Aging 35, 746-756.

Slifer, M. A., Martin, E. R., Bronson, P. G., Browning-Large, C., Doraiswamy, P.M., Welsh-Bohmer, K. A., et al. (2006). Lack of association between UBQLN1 and Alzheimer disease. Am. J. Med. Genet. B Neuropsychiatr. Genet. 141B, 208-213.

Swerdlow, R. H. (2011). Brain aging, Alzheimer's disease, and mitochondria. Biochim. Biophys. Acta 1812, 1630-1639.

Swingler TE, et al. (2012) The expression and function of microRNAs in chondrogenesis and osteoarthritis. Arthritis Rheum 64(6):1909-1919.

Tampellini, D., and Gouras, G. K. (2010). Synapses, synaptic activity and intraneuronal abeta in Alzheimer's disease. Front. Aging Neurosci. 2:13.

Tan L, et al. (2014) Circulating miR-125 as a biomarker of Alzheimer's disease. J Neurol Sci 336(1-2):52-56.

Terry, R. D., Masliah, E., Salmon, D. P., Butters, N., DeTeresa, R., Hill, R., et al. (1991). Physical basis of cognitive alterations in Alzheimer's disease: synapse loss is the major correlate of cognitive impairment. Ann. Neurol. 30, 572-580.

Tóth, M. E., Szegedi, V., Varga, E., Juhász, G., Horváth, J., Borbély, E., et al. (2013). verexpression of Hsp27 ameliorates symptoms of Alzheimer's disease in APP/PS1 mice. Cell Stress Chaperones 18, 759-771.

Vallortigara, J., Whitfield, D., Quelch, W., Alghamdi, A., Howlett, D., Hortobágyi, T., et al. (2016). Decreased levels of VAMP2 and monomeric alphasynuclein correlate with duration of dementia. J. Alzheimers Dis. 50, 101-110.

von Bernhardi R, et al. (2015) Role of TGFβ signaling in the pathogenesis of Alzheimer's disease. Front Cell Neurosci 9:426.

Wang N, et al. (2015) Profiling and initial validation of urinary microRNAs as biomarkers in IgA nephropathy. PeerJ 3: e990.

Wilcock, D. M., Hurban, J., Helman, A. M., Sudduth, T. L., McCarty, K. L., Beckett, T. L., et al. (2015). Down syndrome individuals with Alzheimer's disease have a distinct neuroinflammatory phenotype compared to sporadic Alzheimer's disease. Neurobiol. Aging 36, 2468-2474.

Williams, J. et al. (2016). Are microRNAs true sensors of ageing and cellular senescence?. Ageing Res. Rev. 35, 350-363.

World Alzheimer Report (2015). Publication Alzheimer's Association.

Xie K, et al. (2013) Tenascin-C deficiency ameliorates Alzheimer's disease-related pathology in mice. Neurobiol Aging 34(10):2389-2398.

Yan S, et al. (2017) Altered microRNA profiles in plasma exosomes from mesial temporal lobe epilepsy with hippocampal sclerosis. Oncotarget 8(3):4136-4146.

Zafari S, et al. (2015) Circulating biomarkers panels in Alzheimer's disease. Gerontology 61(6):497-503.

Zhang H, et al. (2015) MicroRNA-455 regulates brown adipogenesis via a novel HIF1an-AMPK-PGC1α signaling network. EMBO Rep 16(10):1378-1393.

Zhang Z, et al. (2015) MiR-455-3p regulates early chondrogenic differentiation via inhibiting Runx2. FEES Lett 589 (23):3671-3678.

Zhao Y, et al. (2015) microRNA-based biomarkers and the diagnosis of Alzheimer's disease. Frontiers in Neurology 6:162.

Zhao, Y., Yan, M., Yun, Y., Zhang, J., Zhang, R., Li, Y., et al. (2017). MicroRNA455-3p functions as a tumor suppressor by targeting eIF4E in prostate cancer. Oncol. Rep. 37, 2449-2458.

Zheng J, et al. (2016) MicroRNA455-3p Inhibits Tumor Cell Proliferation and Induces Apoptosis in HCT116 Human Colon Cancer Cells. Med Sci Monit 22:4431-4437.

Zheng, J., Lin, Z., Zhang, L., and Chen, H. (2016). MicroRNA455-3p inhibits tumor cell proliferation and induces apoptosis in HCT116 human colon cancer cells. Med. Sci. Monit. 18, 4431-4437.

Zhu, X., Perry, G., Smith, M. A., and Wang, X. (2013). Abnormal mitochondrial dynamics in the pathogenesis of Alzheimer's disease. J. Alzheimers Dis. 33, S253-S262.

International Search Report and Written Opinion PCT/US2018/041840 [ISA/AU] dated Oct. 17, 2018.

Bernier, Francois et al. "Recent Progress in the Identification of Non-Invasive Biomarkers to Support the Diagnosis of Alzheimer's Disease in Clinical Practice and to Assist Human Clinical Trials" In: "Alzheimer's Disease—Challenges for the Future", Jul. 1, 2015.

Extended European Search Report, EP 18832682.1 dated Mar. 11, 2021.

\* cited by examiner

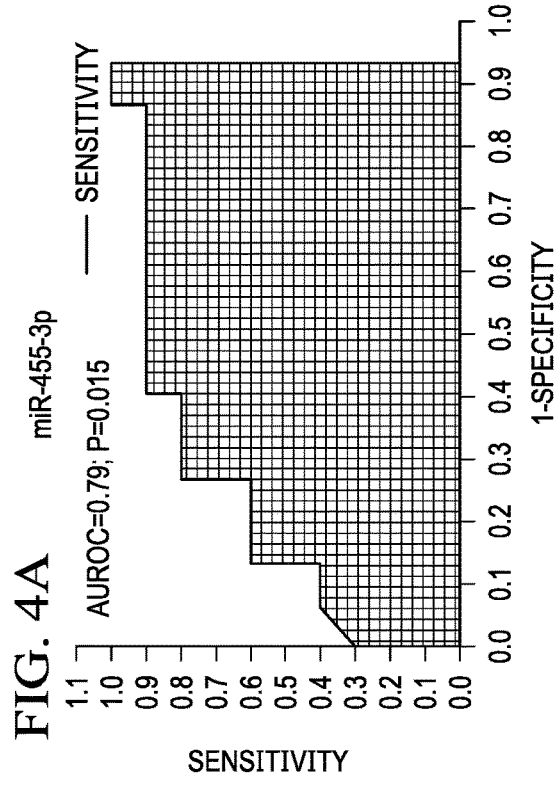
FIG. 3E
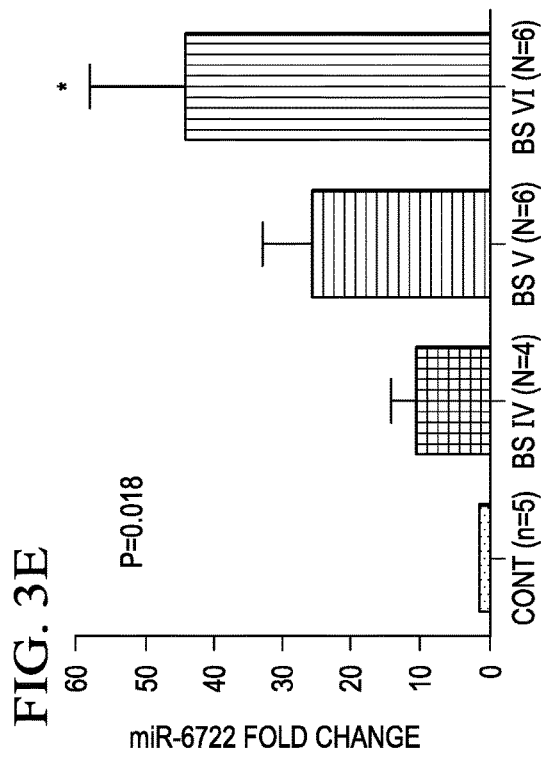
FIG. 4A
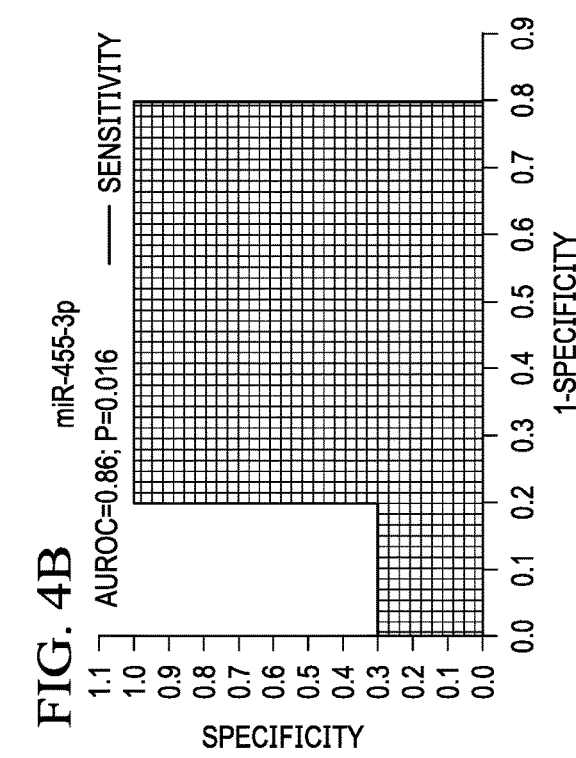
FIG. 4B
FIG. 5A

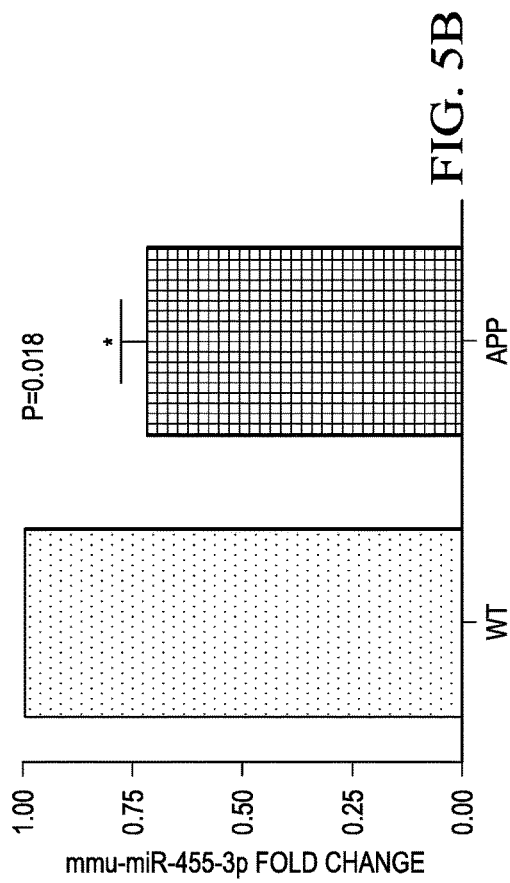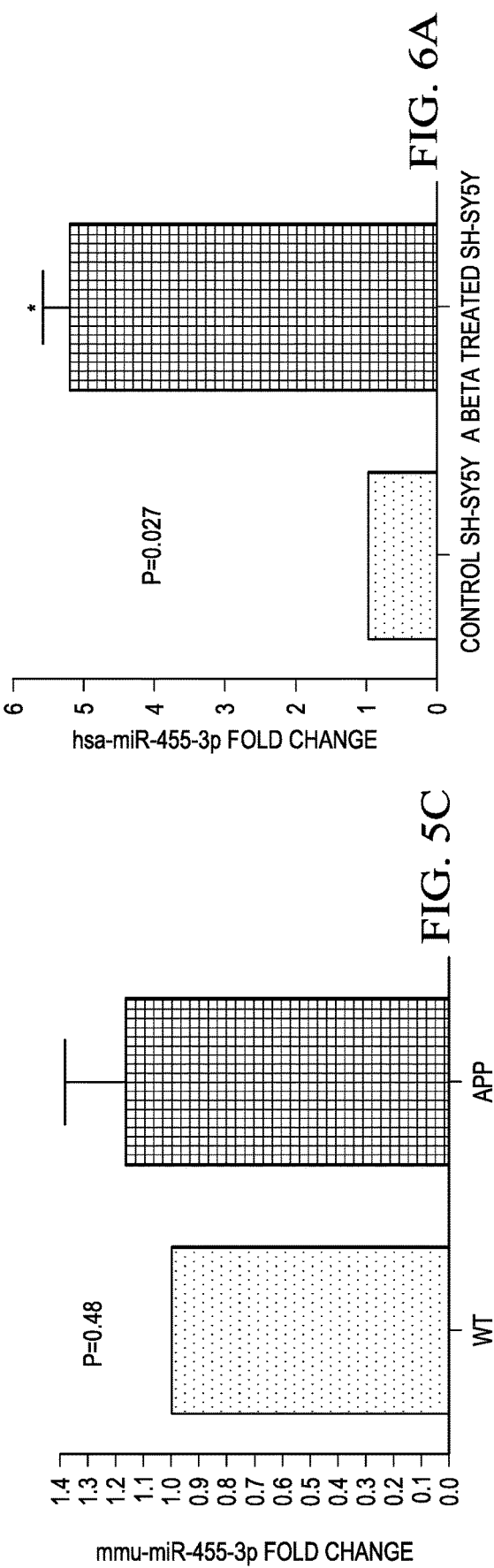

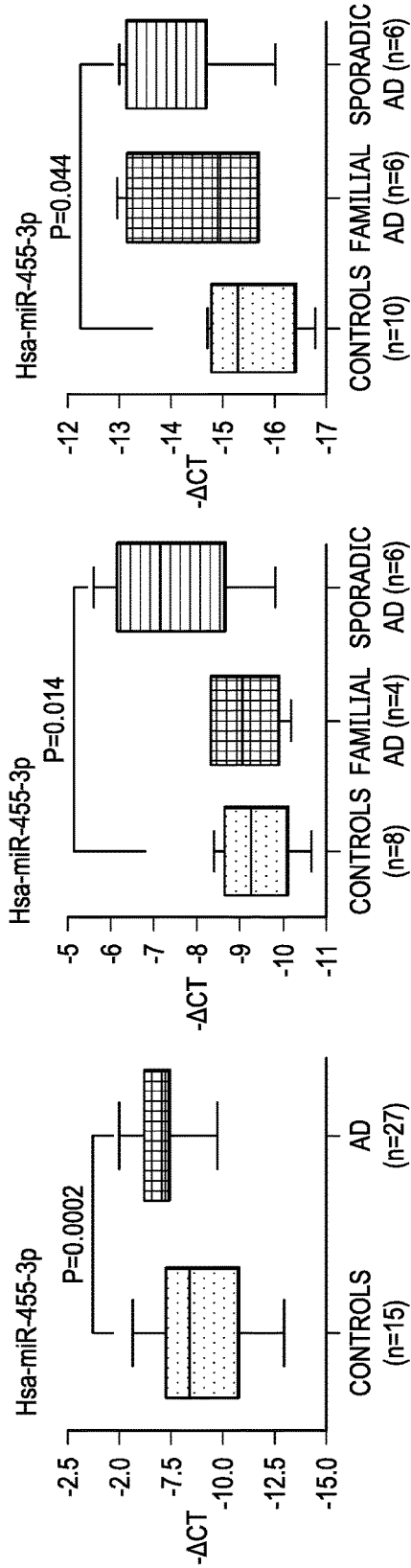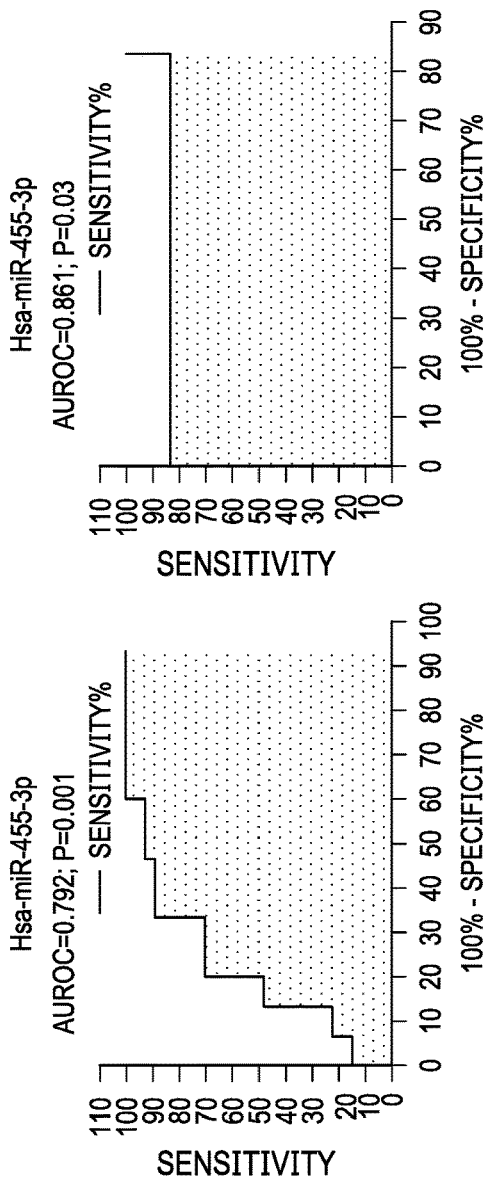
FIG. 10A, FIG. 10B, FIG. 10C, FIG. 11A, FIG. 11B, FIG. 11C

MICRORNA-455-3P AS A PERIPHERAL BIOMARKER FOR ALZHEIMER'S DISEASE

CROSS-REFERENCE TO RELATED APPLICATIONS

This application is the National Stage of International Application No. PCT/US2018/041840, filed on Jul. 12, 2018 claiming the priority of U.S. Provisional Application No. 62/531,760, filed on Jul. 12, 2017, the content of each of which is incorporated by reference herein.

TECHNICAL FIELD OF THE INVENTION

The present invention relates in general to the field of biomarkers for Alzheimer's Disease.

INCORPORATION-BY-REFERENCE OF MATERIALS FILED ON COMPACT DISC

The present application includes a Sequence Listing, which has been submitted in ASCII format via EFS-Web and is hereby incorporated by reference in its entirety. Said ASCII copy, created on Jul. 12, 2018, is named TECH2106WO_SeqList and is 3 kilobytes in size.

BACKGROUND OF THE INVENTION

Without limiting the scope of the invention, its background is described in connection with biomarkers for Alzheimer's Disease.

One such invention is taught in U.S. Pat. No. 9,188,595, issued to Zhao, et al., and entitled "Alzheimer's disease diagnosis based on mitogen-activated protein kinase phosphorylation." Briefly, these inventors teach a method of diagnosing Alzheimer's disease in a patient by determining whether the phosphorylation level of an indicator protein in cells of the patient after stimulus with an activator compound is abnormally elevated as compared to a basal phosphorylation level, the indicator protein being e.g. Erk1/2 and the activator compound is bradykinin.

Another invention is taught in United States Patent Publication No. 20140378439, filed by Derso, et al., entitled "MicroRNA Biomarkers Indicative Of Alzheimer's Disease." These inventors are said to teach a method of diagnosing Alzheimer's Disease in a subject, by determining the level of at least one miRNA in a sample derived from the subject, wherein a change in the level of the at least one miRNA relative to a suitable control is indicative of Alzheimer's Disease in the subject. Methods for monitoring the course of Alzheimer's Disease, methods of treating a subject having Alzheimer's Disease, and kits for diagnosing Alzheimer's Disease are also said to be taught.

Yet another invention is taught in United States Patent Publication No. 20140302068, filed by Khoo, et al., entitled "MicroRNA Biomarkers for Diagnosing Parkinson's Disease", which is said to teach the identification, development and validation of plasma-based circulating microRNA (miRNAs) biomarkers useful in determining if a subject has Parkinson's disease (PD), is at increased risk of developing PD, or has PD that is progressing or is in remission.

Another such invention is taught in United States Patent Publication No. 20140031245, filed by Khan, et al., and entitled "Alzheimer's Disease-Specific Alterations Of The Erk1/Erk2 Phosphorylation Ratio-Alzheimer's Disease-Specific Molecular Biomarkers (ADSMB)". Briefly, these applicants are said to teach methods of diagnosing Alzheimer's Disease as well as to methods of confirming the presence or absence of Alzheimer's Disease in a subject. These application methods of identifying a lead compound useful for the treatment of Alzheimer's Disease by contacting non-Alzheimer's cells with an amyloid beta peptide, stimulating the cells with a protein kinase C activator, contacting the cells with a test compound, and determining the value of an Alzheimer's Disease-specific molecular biomarker. The invention is also said to be directed to kits containing reagents for the detection and diagnosis of the presence or absence of Alzheimer's Disease using the Alzheimer's Disease-specific molecular biomarkers disclosed.

Yet another invention is taught in International Patent Publication No. WO2009009457A1, filed by Wang, et al., entitled "Alzheimer's disease-specific micro-RNA microarray and related methods." These inventors are said to disclosed the diagnosis and/or prognosis of Alzheimer's disease in subjects by measuring amounts of one or more micro-RNAs correlated with Alzheimer's disease present in a biological sample, including blood for example, from a subject.

Despite the prior art disclosures, compositions and methods to detect Alzheimer's disease (AD) early, before clinical symptoms develop, are urgently needed to intervene as soon as possible in disease progression. Also needed are early peripheral microRNA (miRNA) biomarkers for AD.

SUMMARY OF THE INVENTION

In one embodiment, the present invention includes a method for identifying a Alzheimer's disease (AD) patient prior to reaching clinical disease classification, comprising: obtaining a dataset associated with a blood, serum, or plasma sample from the patient, wherein the dataset comprises data representing the level of one or more microRNA biomarkers in the blood, serum, or plasma sample; assessing the dataset for a presence or an increase in an amount of miRNA-445-3p; determining the likelihood that the patient will develop AD patient prior to reaching clinical disease classification by detecting the presence or the increase in miRNA-445-3p to produce a score that is indicative of a likelihood of developing AD, wherein a higher score relative to a healthy control indicates that the patient is likely to have the prognosis for transitioning to classified AD, wherein the healthy control is derived from a non-AD patient with no clinical evidence of AD. In one aspect, the method further comprises administering an anti-AD treatment to the patient prior to reaching clinical disease classification, wherein the anti-AD treatment targets one or more proteins in a KEGG molecular pathway. In another aspect, the method further comprises administering a cyclooxygenase inhibitor, a Catecholamine transferase inhibitor, a protein kinases inhibitor, a Neurotransmitter transporter inhibitor, a Renin-angiotensin system inhibitor, a EGFR tyrosine kinase inhibitor, or a HMG-CoA reductase inhibitor. In another aspect, the patient is identified at least 0.1, 0.9, 2.0, 3.5, or greater than 3.5 years prior to reaching clinical disease classification. In another aspect, the step of assessing comprises RT-PCR, qRT-PCR, biochip, singleplexed or multiplexed RT-PCR. In another aspect, the method further comprises assessing at least one additional biomarker selected from: hsa-miR-3613-3p and hsa-miR-4668-5p, which is up-regulated. In another aspect, the method further comprises assessing at least one additional biomarker selected from: hsa-mir-320d-2, hsa-miR-378h, hsa-miR-3921, hsa-miR-6805-5p, hsa-miR-92a-3p, hsa-miR-3613-5p, which is down-regulated. In another aspect, the method further comprises obtaining the dataset associated with the sample comprises obtaining the sample and processing the sample to experimentally determine the dataset, or wherein obtaining the dataset associated with the sample comprises receiving the dataset from a third party that has processed the sample to experimentally determine the dataset. In another aspect, the method further comprises identifying a relative of the patient at risk for AD by obtaining a score from a dataset associated with a blood, serum, or plasma sample from a relative of the AD patient prior to reaching clinical disease classification. In another aspect, the healthy control is a pre-determined average level derived from a healthy individual with no clinically documented evidence of AD. In another aspect, the miR-455-3p has a greater that 20-fold increase in expression in Braak stage V and VI compared to controls. In another aspect, the expression of miR-3613-3p is higher in the brain tissues at Braak stage V when compared to controls. In another aspect, the expression of MiR-4674 is higher in the postmortem brains from AD patients at the Braak stages IV and V, and significantly higher at stage VI compared to controls. In another aspect, the expression of miR-4668-5p up-regulated in AD brains at Braak stages IV, V, and VI, but less than miR-455-3p or MiR-4674. In another aspect, the expression of mir-6722 was down-regulated in AD serum samples Braak stages I to III, but increased in the AD patients at Braak stage VI, V, and VI. In another aspect, the upregulation of miR-455-3p was significantly higher in postmortem brains from AD patients at Braak stage V having a ApoE (3/4) genotype when compared to controls. In another aspect, the Braak stage can be differentiated between Stage I to III versus Brask Stage IV to VI by comparing the expression of miR-455-3p, miR-3613-3p, miR-4668-5p, and mir-6722.

In another embodiment, the present invention includes a method for assessing a patient prior to reaching AD clinical disease classification comprising: (a) obtaining a blood, serum, or plasma sample from the AD patient; (b) obtaining a dataset of biomarkers from the blood, serum, or plasma sample from the AD patient, wherein the dataset comprises data representing the level of one or more biomarkers to determine a pre-classification soluble mediator score, wherein at least one biomarker is selected: assessing the dataset for a presence or an increase in an amount of miRNA-445-3p; determining the likelihood that the patient will develop AD patient prior to reaching clinical disease classification by detecting the presence or the increase in miRNA-445-3p to produce a score that is indicative of a likelihood of developing AD, wherein a higher score relative to a healthy control indicates that the patient is likely to have the prognosis for transitioning to classified AD, wherein the healthy control is derived from a non-AD patient with no clinical evidence of AD. In one aspect, the method further comprises administering a treatment to the AD patient prior to reaching clinical disease classification after determining that the patient has the prognosis for transitioning to classified AD, wherein the treatment comprises and anti-AD therapy. In another aspect, the method further comprises administering a cyclooxygenase inhibitor, a Catecholamine transferase inhibitor, a protein kinases inhibitor, a Neurotransmitter transporter inhibitor, a Renin-angiotensin system inhibitor, a EGFR tyrosine kinase inhibitor, or a HMG-CoA reductase inhibitor. In another aspect, the method further comprises assessing at least one additional biomarker selected from: hsa-miR-3613-3p and hsa-miR-4668-5p, which is up-regulated. In another aspect, the method further comprises assessing at least one additional biomarker selected from: hsa-mir-320d-2, hsa-miR-378h, hsa-miR-3921, hsa-miR-6805-5p, hsa-miR-92a-3p, hsa-miR-3613-5p, which is down-regulated. In another aspect, the patient is identified at least 0.1, 0.9, 2.0, 3.5, or greater than 3.5 years prior to reaching clinical disease classification. In another aspect, the step of assessing comprises RT-PCR, qRT-PCR, biochip, singleplexed or multiplexed RT-PCR.

In yet another embodiment, the present invention includes a method for identifying an Alzheimer's Disease (AD) patient prior to reaching clinical disease classification comprising: obtaining a blood, serum, or plasma sample from the AD patient; assessing the dataset for a presence or an increase in an amount of miRNA-445-3p; determining the likelihood that the patient will develop AD patient prior to reaching clinical disease classification by detecting the presence or the increase in miRNA-445-3p to produce a score that is indicative of a likelihood of developing AD, wherein a higher score relative to a healthy control indicates that the patient is likely to have the prognosis for transitioning to classified AD, wherein the healthy control is derived from a non-AD patient with no clinical evidence of AD; and administering a treatment to the AD patient prior to reaching clinical disease classification after determining that the patient has the prognosis for transitioning to classified AD, wherein the treatment comprises and anti-AD therapy. In one aspect, the method further comprises administering a cyclooxygenase inhibitor, a Catecholamine transferase inhibitor, a protein kinases inhibitor, a Neurotransmitter transporter inhibitor, a Renin-angiotensin system inhibitor, a EGFR tyrosine kinase inhibitor, or a HMG-CoA reductase inhibitor. In another aspect, the step of assessing comprises RT-PCR, qRT-PCR, biochip, singleplexed or multiplexed RT-PCR. In another aspect, the method further comprises assessing at least one additional biomarker selected from: hsa-miR-3613-3p and hsa-miR-4668-5p, which is up-regulated. In another aspect, the method further comprises assessing at least one additional biomarker selected from: hsa-mir-320d-2, hsa-miR-378h, hsa-miR-3921, hsa-miR-6805-5p, hsa-miR-92a-3p, hsa-miR-3613-5p, which is down-regulated. In another aspect, the dataset associated with the sample comprises obtaining the sample and processing the sample to experimentally determine the dataset, or wherein obtaining the dataset associated with the sample comprises receiving the dataset from a third party that has processed the sample to experimentally determine the dataset. In another aspect, the method further comprises identifying a relative of the patient at risk for AD by obtaining a score from a dataset associated with a blood, serum, or plasma sample from a relative of the AD patient prior to reaching clinical disease classification. In another aspect, the healthy control is a pre-determined average level derived from a healthy individual with no clinically documented evidence of AD.

In another embodiment, the present invention includes a method of evaluating a candidate drug believed to be useful in treating AD, the method comprising: (a) obtaining a blood, serum, or plasma sample; (b) assessing the sample for a presence or an increase in an amount of miRNA-445-3p; (c) administering a candidate drug to a first subset of the patients, and a placebo to a second subset of the patients; (d) repeating step (a) after the administration of the candidate drug or the placebo; and e) determining if the candidate drug reduces the available miRNA-445-3p in the blood, serum, or plasma sample, wherein a decrease that is statistically significant as compared to any reduction occurring in the second subset of patients, wherein a statistically significant reduction indicates that the candidate drug is useful in treating said disease state.

In another embodiment, the present invention includes a composition comprising a recombinant anti-miRNA-445-3p nucleic acid sufficient to knockdown the expression of miRNA-445-3p.

In yet one embodiment, the present invention includes a method of treating a subject in need of therapy for Alzheimer's Disease comprising: identifying a subject suspected of having Alzheimer's Disease; and providing the subject with an effective amount of a recombinant anti-miRNA-445-3p nucleic acid sufficient to knockdown the expression of miRNA-445-3p.

DESCRIPTION OF THE DRAWINGS

For a more complete understanding of the features and advantages of the present invention, reference is now made to the detailed description of the invention along with the accompanying figures and in which:

FIGS. 3A to 3E show qRT-PCR analysis of AD postmortem brains. Specificity and Expression of (FIG. 3A) miR-455-3p, (FIG. 3B) miR-3613-3p, (FIG. 3C) miR-4674, (FIG. 3D) miR-4668-5p and (FIG. 3E) mir-6722 in AD postmortem brain tissues at Braak Stages (BS) IV, V and VI. Fold change was calculated by $2^{-\Delta\Delta ct}$ method. Significant difference among groups were calculated by one-way ANOVA with $P<0.05$ is considered statistically significant.

FIGS. 4A and 4B show the specificity and sensitivity analysis. ROC curve analysis of miR-455-3p in (FIG. 4A) serum samples from AD patients and (FIG. 4B) AD postmortem brain tissue samples.

FIGS. 5A to 5C show qRT-PCR analysis of miR-455-3p in mice model. mmu-miR-455-3p expression in (FIG. 5A) Cerebral cortex, (FIG. 5B) Cerebellum and (FIG. 5C) Serum of APP-mice compared to wild type mice. Fold change was calculated by $2^{-\Delta\Delta ct}$ method. Significant difference among groups were calculated by paired t-test with two-tailed $P<0.05$ is considered significant.

FIGS. 6A and 6B show MiR-455-3p expression in cell lines. qRT-PCR analysis of hsa-miR-455-3p expression in (FIG. 6A) SHSY-5Y cells, and (FIG. 6B) mmu-miR-455-3p expression in N2a cells. Fold change was calculated by $2^{-\Delta\Delta ct}$ method. Significant difference among groups were calculated by paired t-test with two-tailed $P<0.05$ is considered significant.

FIGS. 10A to 10C show that expression of hsa-miR-455-3p in AD patients. (FIG. 10A) miR-455-3p expression in the postmortem brains of healthy controls (n=15) and AD patients' (n=32) was quantified by real-time RT-PCR. Data are presented as "–delta CT" values using box and whiskers plots. Significant difference between groups were calculated by unpaired t-test with $P<0.05$ is considered statistically significant. (FIG. 10B) Expression of hsa-miR-455-3p in human fibroblast cells from healthy controls (n=8), Familial AD cases (n=4) and sporadic AD patients' (n=6). Significant difference between groups were calculated by one-way ANOVA with $P<0.05$ is considered statistically significant. (FIG. 10C) Expression of hsa-miR-455-3p in human B-lymphocytes cells from healthy controls (n=10), Familial AD cases (n=6) and sporadic AD patients' (n=6). Significant difference between groups were calculated by one-way ANOVA with $P<0.05$ is considered statistically significant.

FIGS. 11A to 11C show that ROC curve analysis of hsa-miR-455-3p in (FIG. 11A) AD postmortem brains, (FIG. 11B) AD fibroblast cell lines, and in (FIG. 11C) B-lymphocytes cells from AD patients. The curve was plotted based on the 1CT value of miR-455-3p in AD patients and control samples. Area under the ROC curve (AUROC) was calculated along with the sensitivity and specificity values. $P<0.05$ is considered statistically significant.

DESCRIPTION OF THE INVENTION

Figure 1:
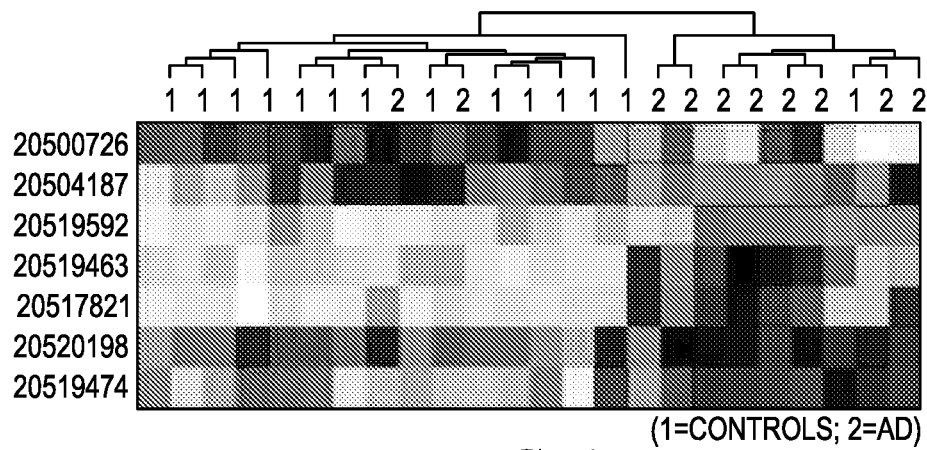
FIG. 1 is a heat map showing hierarchical clustering of miRNAs in AD patients and healthy controls. Left side showed the Transcript cluster ID of differentially expressed 7 miRNAs. Red and green color indicated high and low expression intensities.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

Alzheimer's disease (AD) is progressive neurological disorder affecting aged humans (1). The loss of memory, thinking skills, reasoning abilities, and changes in personality and in behavior are the main characteristics of AD (2). Currently, over 46.8 million people worldwide, including 5.4 million Americans, live with AD-related dementia, and this number is estimated to increase to 131.5 million by 2050 (2). The major pathological hallmarks of AD are the formation of extracellular amyloid plaques and intracellular neurofibrillary tangles (NFTs) in brains of patients with AD. The amyloid plaques accumulate due to the overproduction of the amyloid β peptide (Aβ). This overproduction is due to endoproteolysis of the parental amyloid precursor protein (APP), which is cleaved by the enzyme complexes α-, β-, and γ-secretases (3). Increased production and reduced clearance of Aβ in the brain, may lead to a cascade of events in disease process, including synaptic damage, hyperphosphorylated tau (p-tau), mitochondrial structural and functional changes, inflammatory responses, hormonal imbalance, cell cycle changes, and neuronal loss (4-6).

Currently, to diagnose AD, several biochemical tests are used to detect Aβ and p-tau proteins in the cerebrospinal fluid (CSF) of AD patients. This fluid then undergoes biochemical and molecular tests, to determine the levels of biomarkers of AD. In the CSF of patients diagnosed with AD, the concentration of $A\beta_{(1-42)}$ has been found to be 40-50% lower than concentration levels in individuals who do not have AD (6). Such lower levels of $A\beta_{(1-42)}$ in patients have been detected at later stages of AD progression, but they have not been detected in patients in early stages of disease progression. The use of CSF analysis to determine levels of $A\beta_{(1-42)}$ is considered a safe procedure, but often times, the patients complain about post-examination headaches (7). CSF examination requires highly skilled persons puncturing the lumbar to remove spinal fluid. Additional testing to diagnose AD uses highly sophisticated neuroimaging techniques, such as positron emission tomography and structural magnetic resonance imaging and scanning (8).

Neurodegenerative diseases such as Alzheimer's (AD) and Parkinson's are very debilitating diseases. While the cause of Alzheimer's disease is not known, it is generally accepted that a build up of beta-amyloid (Aβ) plaques in the brain cause the interruption of signaling pathways. This build up of beta-amyloid (Aβ) plaques causes memory problems, language difficulties, mood swings, and other debilitating symptoms. While there is no cure for Alzheimer's disease, early detection of the disease leads to a better prognosis.

Example 1

The primary subject matter of the disclosed invention includes the use of MicroRNAs (miRNAs) found in the blood serum to detect the presence or predict future presence of AD. MicroRNAs are small segments of RNA that are a recent discovery and are currently being heavily researched. Generally, miRNAs are utilized by the body to regulate certain functions. It has been proposed that miRNAs might be useful as biomarkers for detecting disease where there is no other viable method of detection.

In the disclosed technology, miRNA-445-3p has been identified as a biomarker for detecting Alzheimer's disease. The results disclosed herein confirm that when a higher level of miRNA-455-3p is found in a patient's serum, this indicates the presence of Alzheimer's with both high sensitivity and specificity. The miRNA levels of known Alzheimer's patients against non-disease control patients to determine this correlation.

The invention uses miRNA-455-3p as a biomarker for detecting Alzheimer's at its earliest stage. The only current and definitive test for Alzheimer's is postmortem analysis of the brain. With the method disclosed herein, a single blood sample would be capable of measuring the circulating levels of miRNA-455-3p. These measurements would allow physicians to more confidently diagnose and detect Alzheimer's in the earliest stages of the disease.

Given these problems with diagnostic tests for AD, in the last decade researchers have focused on developing non-invasive diagnostic tests capable of detecting nucleic acids, particularly microRNA (miRNAs), known to regulate in patients with AD. These miRNAs are small nucleotide molecules (~22-25 measurement unit) that expressed in humans, plants, fungi, bacteria, and some viruses (9). In neurodegenerative diseases like AD, miRNAs have been found to be deregulated in the blood, plasma, serum, CSF, extracellular fluid, and brain tissues of AD patients (10,11).

In humans, miRNAs are believed to be involved in all developmental and pathological processes by regulating gene expression. They achieve this regulation by targeting 3' UTR and binding RNA sequences at 3'UTR in a sequence-specific manner (12). Some miRNAs are tissue-specific and are localized at certain cellular niches, while others are expressed in all tissues and organs of human body. MiRNAs synthesized in the cells and usually modulate mRNA activity of host cells while in several circumstances, miRNAs released from cells are involved in regulating signals for cells-to-cell communication, known as extracellular miRNAs (13). Extracellular miRNAs are secreted from cells via encapsulated exosomes and micro-particles, or they are released with several lipoprotein complexes, such as high-density lipoproteins (HDL), low-density lipoproteins (LDL), and argonaute 2 proteins (13). These extracellular circulatory miRNAs are very stable in blood components. In pathological conditions, such as in persons with AD, concentrations of particular miRNAs are altered (11). However, the inventors still do not have complete understanding of how expressions(s) of miRNAs progress in non-demented elderly individuals to mild cognitive impairment (MCI), and MCI to AD.

Several recent miRNA studies using CSF, serum, plasma and whole blood revealed that circulatory miRNAs as peripheral biomarkers in AD (6,14-22). However, these studies provided information about miRNAs with little or no consensus in all studies. Further, validation of differentially expressed miRNAs using AD postmortem brains is not well done in these studies.

Therefore, a more detailed study on circulatory miRNAs in AD patients and MCI subjects with thorough validation is urgently needed, in order to determine early detectable peripheral biomarkers in AD. In the present study, the inventors screened AD patients, MCI subjects, and healthy controls for circulatory miRNAs in serum samples using an Affymetrix microarray and qRT-PCR validation assay. Further, differentially expressed miRNAs were validated using AD postmortem brains, APP transgenic mice and AD cell lines.

Levels of serum miRNAs. Total RNA was extracted from 40 serum samples, for microarray analysis, the concentration of miRNAs (10-40 nucleotides) and small RNAs (0-257 nucleotides), and the ratio of miRNAs to small RNAs in each sample were analyzed. The RNA levels were calculated by an Agilent 2100 Bioanalyzer (Agilent Technologies). The average concentration of miRNAs in AD patients was 89.1 pg/μl, in MCI subjects, 132.7 pg/μl and in controls was 119.3 pg/μl. The average concentration of small RNAs was 186 pg/μl in AD patients, 248.5 pg/μl in MCI subjects and 240.2 pg/μl in controls. Similarly, the ratios of average miRNAs to small RNAs in the samples were 49.1%, 54.9% and 49.8% in AD patients, MCI subjects and in controls respectively. These results indicated that miRNA output was greater in the MCI subjects.

Primary screening of serum samples to detect miRNAs. AD patients (n=10), MCI subjects (n=16), and controls (n=14) were analyzed for their miRNA microarray expression using the Affymetrix GeneChip miRNA Array, v. 4.0. A total of 6631 genes were detected in all of the serum samples. Of these 6631 genes, 2578 were mature miRNAs that were listed in the miRbase database, and 2025 were the stem-loop precursor miRNAs (pre-miRNAs). The remaining genes belonged to different classes of small RNAs, such as snoRNA (1491), CDBox (319), HAcaBox (155), scaRna (31), and 5.8 s rRNA (10). Of the remaining genes, 22 were spike-in control RNAs that were added externally during the array experiment. Differential miRNA expression in each miRNA was analyzed, on the fold-change intensity of each miRNA (−2 to +2) and each ANOVA P-value (<0.05).

AD patients and healthy controls. Microarray analysis was performed on the samples from the AD patients (n=10) and the controls (n=14) (FIG. 1). The miRNA bi-weight average (log 2) intensity showed significant (P<0.05) deregulation of 7 miRNAs in AD patients compared to controls (Table 1). The miRNA sequences, hsa-miR-455-3p, hsa-miR-3613-3p, hsa-miR-4668-5p, hsa-miR-5001-5p, hsa-miR-4674, and hsa-miR-4741 were up-regulated, while hsa-miR-122-5p was down-regulated. The top miRNA candidate was hsa-miR-455-3p, which showed a remarkably 11.3-fold higher expression in AD patients compared to controls. Other miRNAs were, hsa-miR-3613-3p (3.67-fold), hsa-miR-4668-5p (3.38-fold), and hsa-miR-4674 (5.62-fold) also exhibited the higher levels of fold expression in AD patients. These results identified new miRNA candidates that were not previously identified in AD.

upregulation in MCI subjects, compared to controls. These results suggested that greater number of miRNA deregulation were observed in the initial phases of disease progression.

AD patients, MCI subjects, and healthy controls. To detect disease progression through the differential expression of miRNAs, the inventors compared the differentially expressed miRNAs in the serum samples of AD patients and MCI subjects (n=10 and n=16, respectively) and controls (n=14) at the same time point in disease progression. The miRNAs in each group of serum samples were analyzed in terms of: bi-weight average (log 2) intensity, a fold change of less than −2 or more than 2, and an ANOVA/FDR, P<0.05. Results indicated that a total of 68 miRNAs (32 mature and 36 precursor) were deregulated among three groups of serum samples. Since, present study aimed to identify promising biomarkers for AD progression, the inventors focused on miRNAs, and those expressions are either gradually increased or decreased among three groups. Of the 32 mature miRNAs that were identified, 7 were gradually upregulated: hsa-miR-455-3p, hsa-miR-3613-3p, hsa-miR-4674, hsa-miR-4668-5p, hsa-miR-4317, hsa-miR-3124-3p, and hsa-miR-6856-3p, while one, hsa-miR-1972

TABLE 1

MiRNAs: log2 intensity and fold change in AD patients and controls

| Transcript Cluster ID | miRNA name | AD Bi-weight Average Signal (log2) | AD Standard Deviation | Control Bi-weight Average Signal (log2) | Control Standard Deviation | Fold Change (linear) (AD vs. Control) | ANOVA p-value | FDR p-value | Chromosome |
|---|---|---|---|---|---|---|---|---|---|
| 20504187 | hsa-miR-455-3p | 6.03 | 1.05 | 2.53 | 1.06 | 11.3 | 0.000003 | 0.007 | chr9 |
| 20517821 | hsa-miR-3613-3p | 3 | 1.32 | 1.13 | 0.16 | 3.67 | 0.000014 | 0.012 | chr13 |
| 20519463 | hsa-miR-4668-5p | 3 | 1.5 | 1.25 | 0.42 | 3.38 | 0.000576 | 0.079 | chr9 |
| 20500726 | hsa-miR-122-5p | 2.31 | 1.4 | 4.26 | 1.24 | −3.85 | 0.004833 | 0.198 | chr18 |
| 20520198 | hsa-miR-5001-5p | 3.73 | 0.7 | 2.49 | 0.77 | 2.37 | 0.011848 | 0.263 | chr2 |
| 20519474 | hsa-miR-4674 | 4.48 | 1.37 | 1.99 | 1.05 | 5.62 | 0.013827 | 0.275 | chr9 |
| 20519592 | hsa-miR-4741 | 2.31 | 0.61 | 1.26 | 0.42 | 2.07 | 0.013923 | 0.276 | chr18 |

AD patients and MCI subjects. To compare the intermediate states of disease progression, microarray data were analyzed from the AD patients (n=10) and MCI subjects (n=16). Heat map data and hierarchical clustering showed the differential expressions of 8 miRNA candidates. Based on the bi-weight average (log 2) intensity and linear fold-change values, the miRNAs hsa-miR-3613-3p and hsa-miR-4668-5p were significantly up-regulated (ANOVA, P<0.05) and hsa-mir-320d-2, hsa-miR-378h, hsa-miR-3921, hsa-miR-6805-5p, hsa-miR-92a-3p, hsa-miR-3613-5p were down-regulated in the serum samples of AD patients compared to MCI subjects.

MCI subjects and healthy controls. Microarray data were compared between MCI subjects (n=16) and controls (n=14). Hierarchical clustering showed a wide range of miRNA signatures that were deregulated. Interestingly, 50 miRNAs were identified, and all of them were significantly up-regulated in MCI subjects. Surprisingly, miR-4674 (5.24-fold) and miR-455-3p (5.18-fold) showed maximum was down-regulated in AD and MCI subjects compared to controls. Further, the remaining pre-miRNAs (hsa-mir-124-1, hsa-mir-4417, hsa-mir-1908, hsa-mir-3912, hsa-mir-4325, and hsa-4776-2) showed gradual upregulation while 4 of the pre-miRNAs (hsa-mir-6722, hsa-mir-412, hsa-mir-3153, and hsa-mir-4430) showed gradual downregulation.

Among the 68 miRNAs that the inventors studied, the most significantly unregulated (ANOVA/FDR, P<0.05) were 4 miRNAs miR-455-3p, miR-3613-3p, miR-4674, and miR-4668-5p and the one down-regulated miRNA mir-6722. These miRNAs were selected for secondary screening and validation analysis since their expression varied more in the 3 groups of serum samples (Table 2). The miR-455-3p log 2 intensity showed a 2.53-fold increase in the controls, a 4.9-fold increase in MCI subjects, and a 6.03-fold increase in AD patients. Similarly, the expression of miR-4674 also increased from 1.99-fold in controls, to a 4.38-fold increase in MCI subjects, and to a 4.48-fold increase in AD patients.

TABLE 2 miRNAs: log2 intensity and fold change in AD patients, MCI subjects, and controls

| Transcript Cluster ID | Transcript ID | AD Bi-weight Average Signal (log2) | MCI Bi-weight Average Signal (log2) | Controls Bi-weight Average Signal (log2) | AD SD | MCI SD | Controls SD | ANOVA p-value (All Conditions) | FDR p-value (All Conditions) | Fold Change (linear) (AD vs. MCI) | Fold Change (linear) (AD vs. Controls) | Fold Change (linear) (MCI vs. AD) |
|---|---|---|---|---|---|---|---|---|---|---|---|---|
| 20504187 | hsa-miR-455-3p | 6.03 | 4.9 | 2.53 | 1.05 | 1.29 | 1.06 | 0.000002 | 0.001994 | 2.18 | 11.3 | −2.18 |
| 20537464 | hsa-mir-6722 | 5.72 | 6.27 | 6.72 | 0.45 | 0.48 | 0.4 | 0.000016 | 0.007169 | −1.46 | −1.99 | 1.46 |
| 20519474 | hsa-miR-4674 | 4.48 | 4.38 | 1.99 | 1.37 | 1.26 | 1.05 | 0.000208 | 0.024285 | 1.07 | 5.62 | −1.07 |
| 20517821 | hsa-miR-3613-3p | 3 | 1.25 | 1.13 | 1.32 | 0.64 | 0.16 | 9.42E−07 | 0.001562 | 3.37 | 3.67 | −3.37 |
| 20519463 | hsa-miR-4668-5p | 3 | 1.67 | 1.25 | 1.5 | 0.91 | 0.42 | 0.000711 | 0.045154 | 2.52 | 3.38 | −2.52 |

The miR-4668-5p showed a gradual upregulation of up to 3-fold in AD patients, compared to 1.25-fold increase in controls, and a 1.67-fold increase in MCI subjects. The miR-3613-3p expression also gradually increased when the miRNAs were analyzed and compared in controls, MCI, and AD patients (1.13-fold, 1.25-fold, and 3.0-fold increases, respectively). The expression of mir-6722 gradually decreased in MCI subjects (6.27-fold) and AD patients (5.72-fold) compared to mir-6722 expression (6.72-fold) in controls. Thus, the circulatory serum miRNAs showed aberrant expression in the healthy controls and diseased states (AD and MCI). Also noteworthy was that the level of expression in these molecules consistently either increased or decreased with disease progression. Hence, such miRNAs are capable of discriminating between healthy persons and persons with AD or MCI. Such miRNAs could also be used to monitor disease progression in AD patients.

Figure 2A:
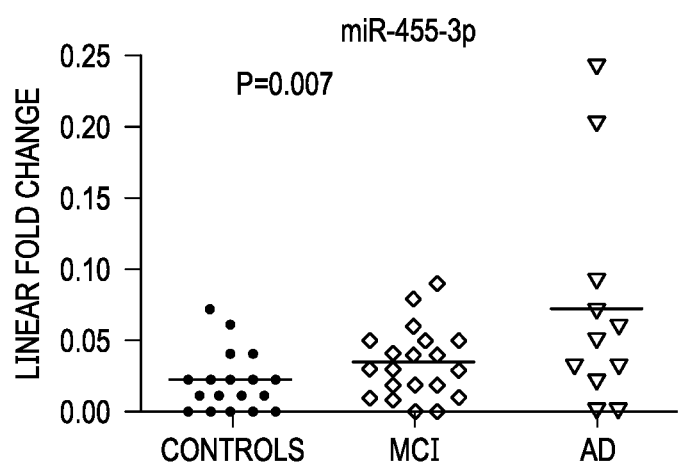
FIGS. 2A to 2E show qRT-PCR validation of serum samples. Expression of (FIG. 2A) miR-455-3p, (FIG. 2B) miR-4668-5p, (FIG. 2C) miR-4674, (FIG. 2D) miR-3613-3p and (FIG. 2E) mir-6722 in healthy controls, MCI subjects and AD patients' serum samples. Fold change was calculated by $2^{-\Delta ct}$ method. Significant difference among groups were calculated by one-way ANOVA with $P<0.05$ is considered statistically significant.
Figure 2B:
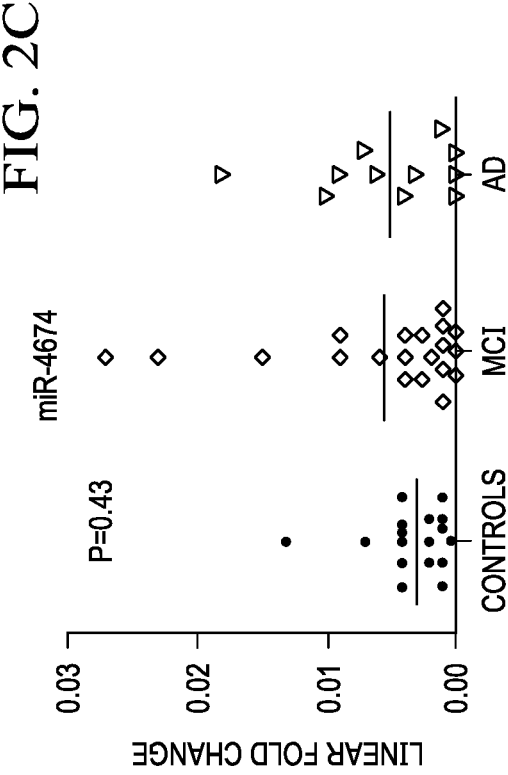
Figure 2C:
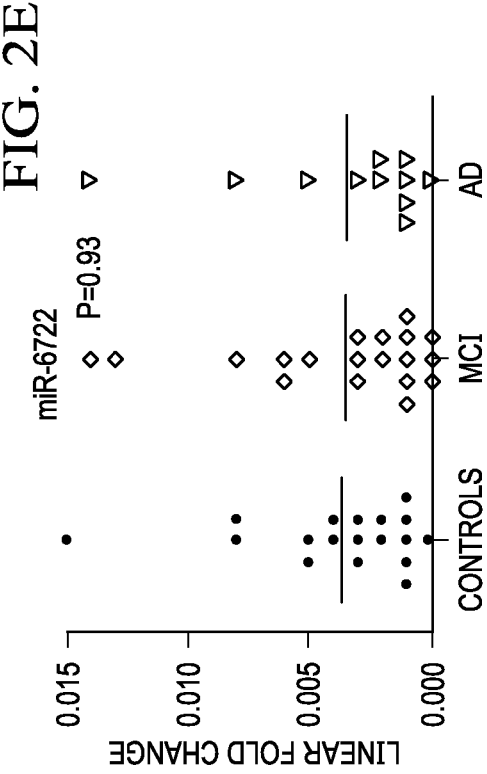
Figure 2D:
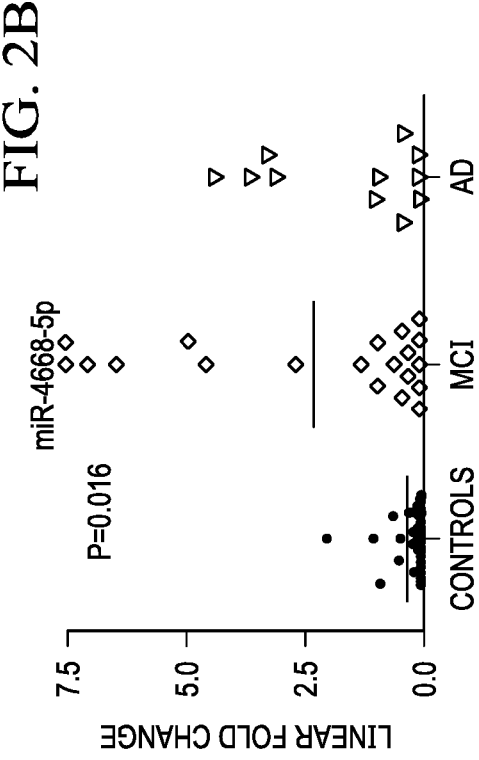

Secondary screening and validation of miRNAs in serum samples. Selected miRNAs (miR-455-3p, miR-3613-3p, miR-4674, miR-4668-5p and mir-6722) were further validated for their expression using qRT-PCR assays. The expression of miR-455-3p was quantified in serum of controls (n=18), MCI subjects (n=20), and AD patients (n=11). Interestingly, fold-change (mean±SD) analysis indicated a gradual upregulation of miR-455-3p in AD patients (0.071±0.078-fold) (P=0.007) compared to the fold-change in MCI subjects (0.034±0.024-fold) and in controls (0.019±0.020-fold) (FIG. 2A). Similarly, the expression of miR-4668-5p was also significantly (P=0.016), upregulated in MCI subjects (2.25±2.78-fold) compared to controls (0.340±0.50-fold) (FIG. 2B). However, miR-4668-5p expression did not show significant elevation in the AD patient's serum (1.50±1.61-fold). In similar way, expressions of miR-4674 and miR-3613-3p also increased in the MCI and AD patients, though it was not significant (FIGS. 2C and 2D).

Figure 2E:
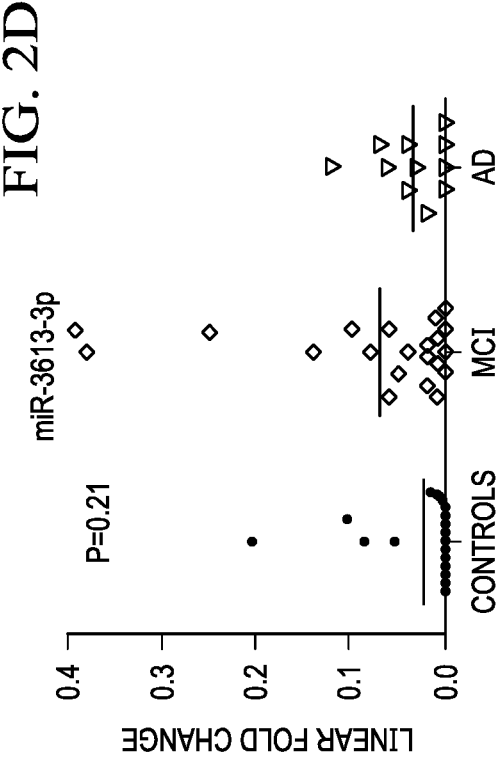

The expression of precursor miRNA (mir-6722) was also quantified by qRT-PCR, with results showing a gradual down regulation in MCI and AD patients compared to controls, but not significantly (FIG. 2E). A microarray-based panel of 5 miRNAs was found to concur with qRT-PCR validation in controls, MCI and AD serum samples. However, a statistical analysis revealed that miR-455-3p and miR-4668-4p were significantly upregulated in persons with AD or MCI from healthy controls.

Figure 3B:
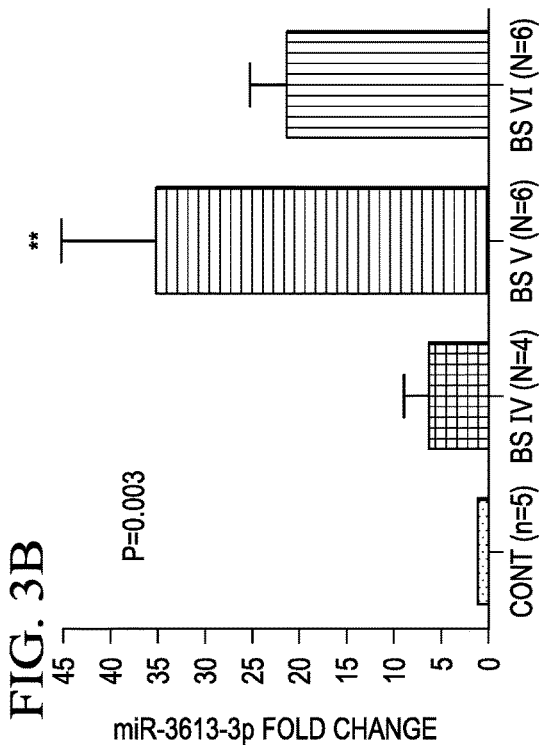
Figure 3D:
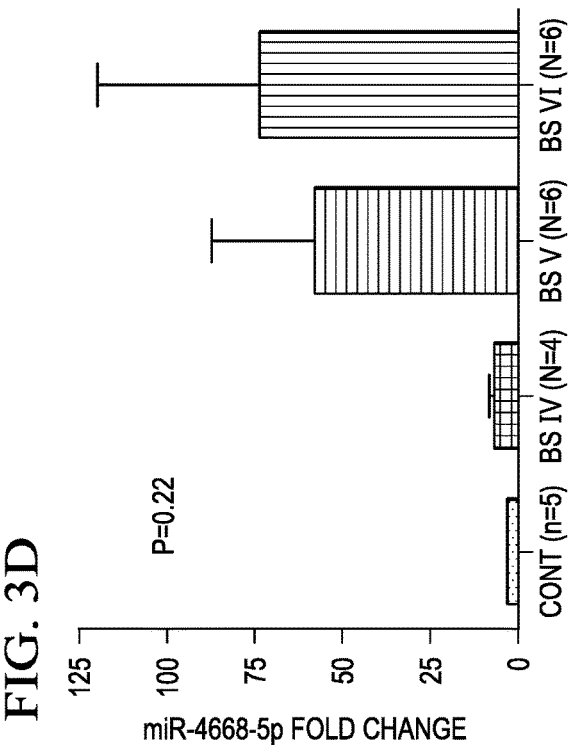
Figure 3A:
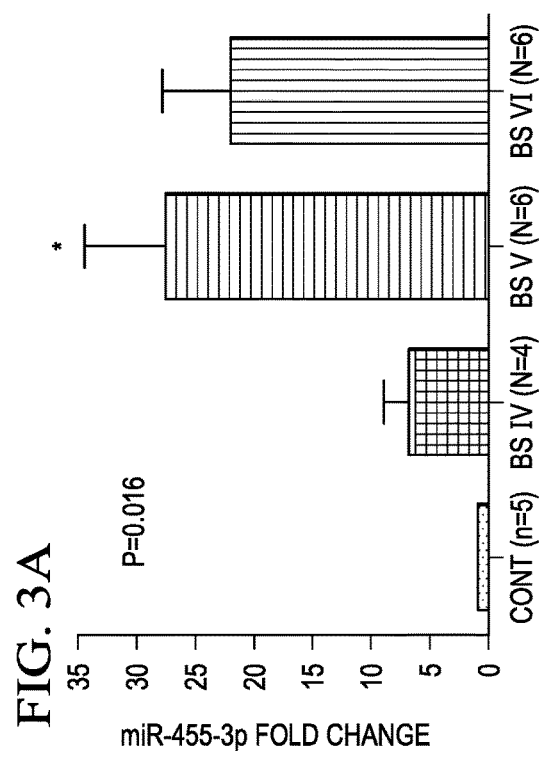

Validation of serum miRNA expressions using AD postmortem brains. Total RNA was isolated from postmortem brains (frontal cortex) of AD patients at Braak stages IV (n=4), V (n=6), and VI (n=6), and in controls (n=5). Expression of selected 5-miRNA panel was quantified by qRT-PCR. The average fold change in each miRNA was higher in AD brains at Braak stages IV, V, and VI compared to the control brains. Expression of miR-455-3p was increased in the AD brains at all Braak stages compared to controls. However, a significant upregulation was observed in brains from AD patients at the Braak stage V (26.59-fold, P=0.016) (FIG. 3A). Similarly, miR-3613-3p expression was also higher in the brain tissues at Braak stage V (P=0.003) compared to controls (FIG. 3B).

Figure 3C:
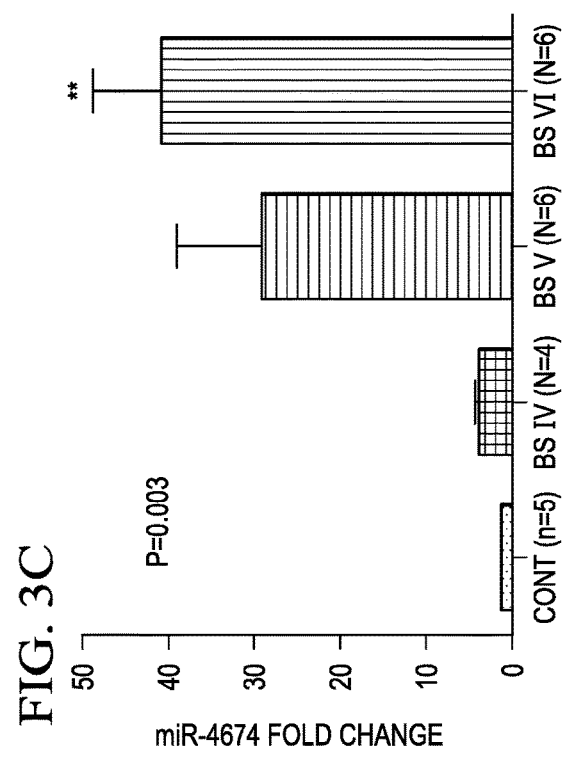

MiR-4674 expression was also higher in the postmortem brains from AD patients at the Braak stages IV and V, but it was significantly higher at stage VI (P=0.003) (FIG. 3C). MiR-4668-5p expression was also up-regulated in AD brains at Braak stages IV, V, and VI, but not the significant level (FIG. 3D). Mir-6722 expression was down-regulated in AD serum samples. However, the expression of mir-6722 was surprisingly increased in the AD patients at Braak stage VI (P=0.018) (FIG. 3E). The opposite facts were observed in the analysis of mir-6722 expression.

The upregulation of miR-455-3p was significant in postmortem brains from AD patients at Braak stage V. Interestingly, those individuals were all having the ApoE (3/4) genotype. The expression of miR-455-3p was the most significantly higher in both the AD serum and AD postmortem brains suggesting that it might be implicated in AD detection and pathogenesis.

Receiver operating characteristics (ROC) curve analysis of miR-455-3p. To determine the diagnostic accuracy using miRNAs in AD patients, ROC curves analysis was studied for miR-455-3p expressions in serum and AD brain samples. The curves were plotted, based on the ΔCt value of miR-455-3p expression in serum samples from the AD patients (n=11) and controls (n=18). Upon analysis, miR-455-3p showed significant area under curve (AUC). The AUROC=0.79 with a 95% confidence interval was 0.59 to 0.98 (P=0.015) in AD serum samples compared to the healthy controls (FIG. 4A). Further, ROC analysis of miR-455-3p expression in postmortem brains from 16 AD patients and 5 healthy controls indicated the significant AUROC value of 0.86 (95% confidence interval was 0.61 to 1.11, P=0.016) (FIG. 4B). Thus, ROC analysis confirmed miR-455-3p as a valuable molecule capable of discriminating persons with and without AD.

Expression of miR-455-3p in APP transgenic mice. Since miR-455-3p showed promising results in terms of its expression in AD serum samples and AD postmortem brains, miR-455-3p expression was also studied in the cortical tissues from an APP transgenic mouse model of AD (Tg2576 line). This study investigated the mmu-miR-455-3p expression in brain tissues from 6-month-old APP mice (n=6) and C57BL/6 wild-type mice (n=6). Total RNA was extracted from disease-affected tissue from the cerebral cortex and non-affected-cerebellum, and mmu-miR-455-3p expression was measured by qRT-PCR. Results showed a 1.8-fold (P=0.004) upregulation of mmu-miR-455-3p in the cerebral cortex tissues of the APP mice, compared to the wild type mice (FIG. 5A). Interestingly, in cerebellum, mmu-miR-455-3p expression was significantly (P=0.018) reduced in the APP mice (FIG. 5B). Expression of mmu-miR-455-3p was also examined in the serum samples from APP mice. Mmu-miR-455-3p expression was higher in the APP mice serum compared to the wild-type mice, although it was not statistically significant (FIG. 5C). A high level of mmu-miR-455-3p expression in the APP mice confirmed a possible role in Aβ-mediated AD pathogenesis.

Figure 6B:
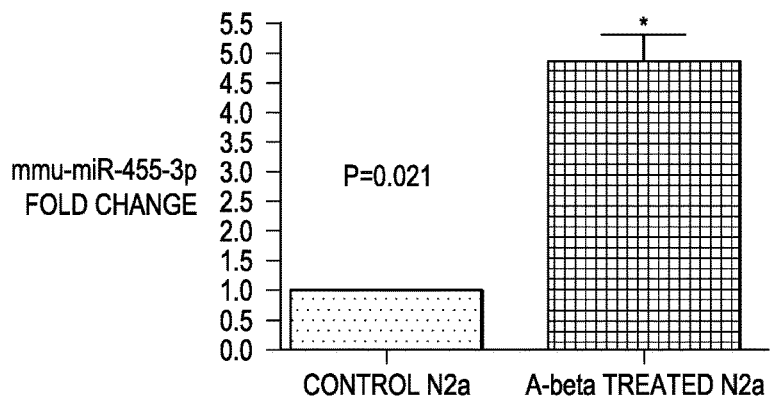

MiR-455-3p expression in $A\beta_{(1-42)}$ treated cells. To determine the effects of the Aβ on the expression of miR-455-3p, the SH-SY5Y (human neuroblastoma) and N2a (mouse neuroblastoma) cells were treated with the $A\beta_{(1-42)}$ peptide (20 µM) for 6 hours. Total intracellular RNA was extracted and expression of human and mouse miR-455-3p were measured by qRT-PCR. Results showed a 4.1-fold (P=0.027) increase in hsa-miR-455-3p expression in the Aβ-treated SH-SY5Y cells compared to control (untreated) cells (FIG. 6A). Similarly, in N2a cells, mmu-miR-455-3p expression was also upregulated by 3.8-fold (P=0.021) in Aβ-treated cells compared to control cells (FIG. 6B). These results further confirmed the significant response of miR-455-3p in Aβ pathologies.

Figure 7:
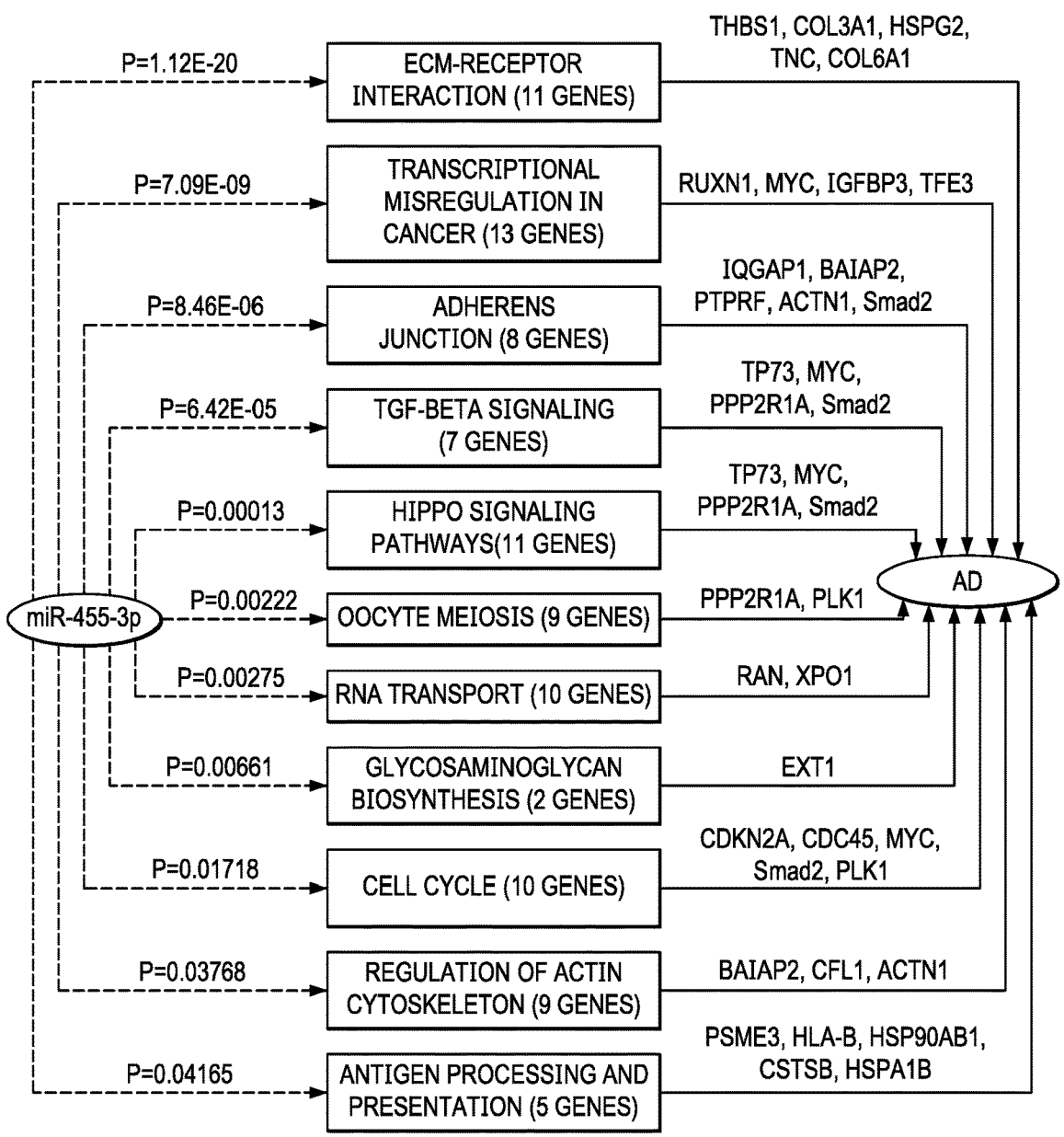
FIG. 7 shows a KEGG pathway analysis of miR-455-3p. MiR-455-3p regulated pathways and target genes were identified using the sources microT-CDS and TarBase to classify KEGG pathway and GO category pathway with $P<0.05$. MiR-455-3p targeted pathway genes identified through literature survey that were implicated in AD pathogenesis.

MiRNA-associated signaling pathways. MiRNA-associated signaling pathways were analyzed using DIANA TOOLS-miRPath algorithm to identify the biological function of these miRNAs and their role in AD pathogenesis. MicroT-CDS files for all five miRNAs were run with a p value <0.05. KEGG pathway analysis unveiled more than 54 biological pathways associated with these miRNAs. This analysis focused on the miR-455-3p and identified possible molecular targets involved in AD pathogenesis. The miRNA analysis identified the relationship of miR-455-3p with 11 biological pathways and associated genes (FIG. 7). The most important signaling pathways were: the ECM-receptor interaction, the adherens junction, the TGF-beta signaling pathway, the hippo signaling pathway, and the regulation of the actin cytoskeleton. These signaling pathways and some of their genes (THBS1, COL3A1, HSPG2, COL6A1, RUXN1, MYC, Smad2, PLK1, and TNC) were directly associated with AD pathogenesis. The upregulation of miR-455-3p in AD development might be associated with the modulation of the above-mentioned genes. Thus, analysis of the signaling pathways revealed a possible molecular mechanism for how miR-455-3p is involved in AD pathogenesis.

Despite the enormous research efforts that have gone into developing ways to diagnose AD at the earliest stages possible, little progress has been made. Perhaps this is at least in partly due to initial research that focused on personal characteristics of persons who developed AD, such as their life style, body mass index, status of AD-related alleles, their genotypic and phenotypic variations, and environmental factors (11,23,24). This research recently broadened the list of potential biomarkers for AD to include blood-based miRNAs, but until the last 5-8 years, little research was actually conducted to narrow the list of miRNAs that might serve as biomarkers for AD, since more than one hundred miRNAs were found to be deregulated in AD patients (6,11,14-21).

The present study narrows the field of miRNAs that might serve as peripheral biomarkers for AD. Using Affymetrix microarray analysis, the inventors identified about 6631 types of small RNAs in the serum of patients with AD and with MCI. Of these, only 2578 were mature, and 2025 were stem-loop precursors of human miRNAs. These numbers of mature miRNAs were almost same as the miRNAs entry on miRbase release 21 (2588 mature) for *Homo sapiens* (www.mirbase.org/cgi-bin/browse.pl). From these results, the inventors came to know that most of genomic miRNAs were present and/or secreted in peripheral circulation. Based on a recent literature of circulatory miRNAs (11), the inventors had expected that disease-specific miRNAs or miRNAs associated with a particular pathological state, such as AD, were differently expressed and released in peripheral circulation (11). When the inventors compared the 3 different study groups in our research (serum from AD patients, MCI subjects and healthy controls), it was found that miRNA expressions of a wide number of miRNAs change, depending on the serum-donor's stage of disease progression. The highest variation of miRNA expressions was found in the patients' serum who were at the initial stage of disease progression, when the diagnosis of these patients went from control to MCI. Hence, disease-specific early physiological changes are crucial for the miRNAs deregulation in cells. Sequencing analysis of serum exosomes unveiled differential expression of 17 miRNAs in the serum from 3 subject groups (17). However, due to low number of MCI subjects (n=11), none of the exosomal miRNA was verified as biomarker for disease progression (17). In present study, five miRNAs (miR-455-3p, miR-4668-5p, miR-3613-3p, miR-4674, and mir-6722) were selected for validation in order to determine potential biomarker. Results showed a remarkable variation of miR-455-3p in AD serum samples, AD postmortem brains and AD mice, suggesting that it is potential biomarker for AD. These five miRNAs are known to have specific regulating roles in different diseases. MiR-455-3p has a role in colon cancer (25) and also participates in chondrogenic differentiation (26) and cartilage development and degeneration (27). In patients with preeclampsia, miR-455-3p was also found to be linked with hypoxia signaling and the regulation of brown adipogenesis via the HIFlan-AMPK-PGC1a signaling network (28,29). In familial amyotrophic lateral sclerosis, downregulation of miR-455-3p expression has been reported in the sera of these patients (30). The roles of miR-3613-3p and miR-4668-5p have been studied in the pathogenesis and progression of IgA nephropathy (31) and in mesial temporal lobe epilepsy (32). In the plasma of AD patients, low levels of miR-3613-3p were detected using RNA sequencing (33). However, current study showed increased levels of miR-3613-3p in the serum samples of AD patients. In hemolysis-free blood plasma from prostatic cancer patients, an increased level of miR-4674 was reported (34). However, role of these miRNAs is not widely reported in AD and other neurodegenerative diseases.

A recent analysis of biofluids (serum, plasma, CSF) from AD patients revealed many miRNA potential biomarkers for AD, such as miR-9, miR-125b, miR-146a, miR-181c, let-7g-5p, and miR-191-5p (11). However, their expression levels and molecular characterizations were not investigated using postmortem brains from AD patients and AD cell and mouse models. Consequently, no miRNA has been identified as the most likely biomarker for AD. In this current study, the inventors analyzed sera and cortices from AD patients found a significant upregulation of miR-455-3p. The inventors attempted to replicate these observations in AD postmortem brains, APP transgenic mice, and AD cell lines. Interestingly, miR-455-3p expression was more significantly up-regulated in the brains and sera from AD patients at Braak stage who had the ApoE (3/4) genotype. These observations unveiled a possible molecular interaction between miR-455-3p and the ApoE4 genotype.

Another significant finding was that APP transgenic mice exhibited Aβ pathologies (35,36) that corresponded to their high expression of miR-455-3p in the disease-affected brain cortex, but not in other brain areas known not to be affected by disease, such as the cerebellum. These findings indicate a possible molecular link between APP processing and miR-455-3p. This hypothesis was further tested on human and mouse neuroblastoma cells treated with toxic $Aβ_{(1-42)}$ peptides which mimics the AD type pathophysiology. Higher expression levels of miR-455-3p in the $Aβ_{(1-42)}$-treated cells further support miR-455-3p as a potential biomarker for AD. This study is the first to identify miR-455-3p as a key molecule expressing biomarker properties for AD.

MiR-455-3p expression is regulated by the transforming growth factor beta (TGF-β) (37), and its level of expression has been found to be induced by TGF-β1, TGF-β3, and activin A in human SW-1353 chondrosarcoma cells and murine C3H10T1/2 cells (28). The TGF-β signaling pathway reported to play a critical role in Aβ processing in patients with AD since reduced TGF-β signaling has been found to be increased in Aβ deposits in patients with AD (38,39).

Through pathway analysis, the KEGG pathway was found to regulate the TGF-β signaling pathway and eleven associated genes by miR-455-3p (FIG. 7). As a consequence, miR-455-3p is interconnected with TGF-β signaling and Aβ synthesis, and hence, may play a crucial role in AD pathogenesis. MiR-455-3p might also have a major regulatory role in other cellular pathways through modulation of their genes in AD pathogenesis (FIG. 7). It is possible that miR-455-3p may be involved in AD progression through altered expressions of HSPG2, THBS1, COL3A1, COL6A1, TNC, MYC, Smad2, RAN, PLK1, TP73, ACTN1, and IQGAP1 genes (39-47).

Figure 8:
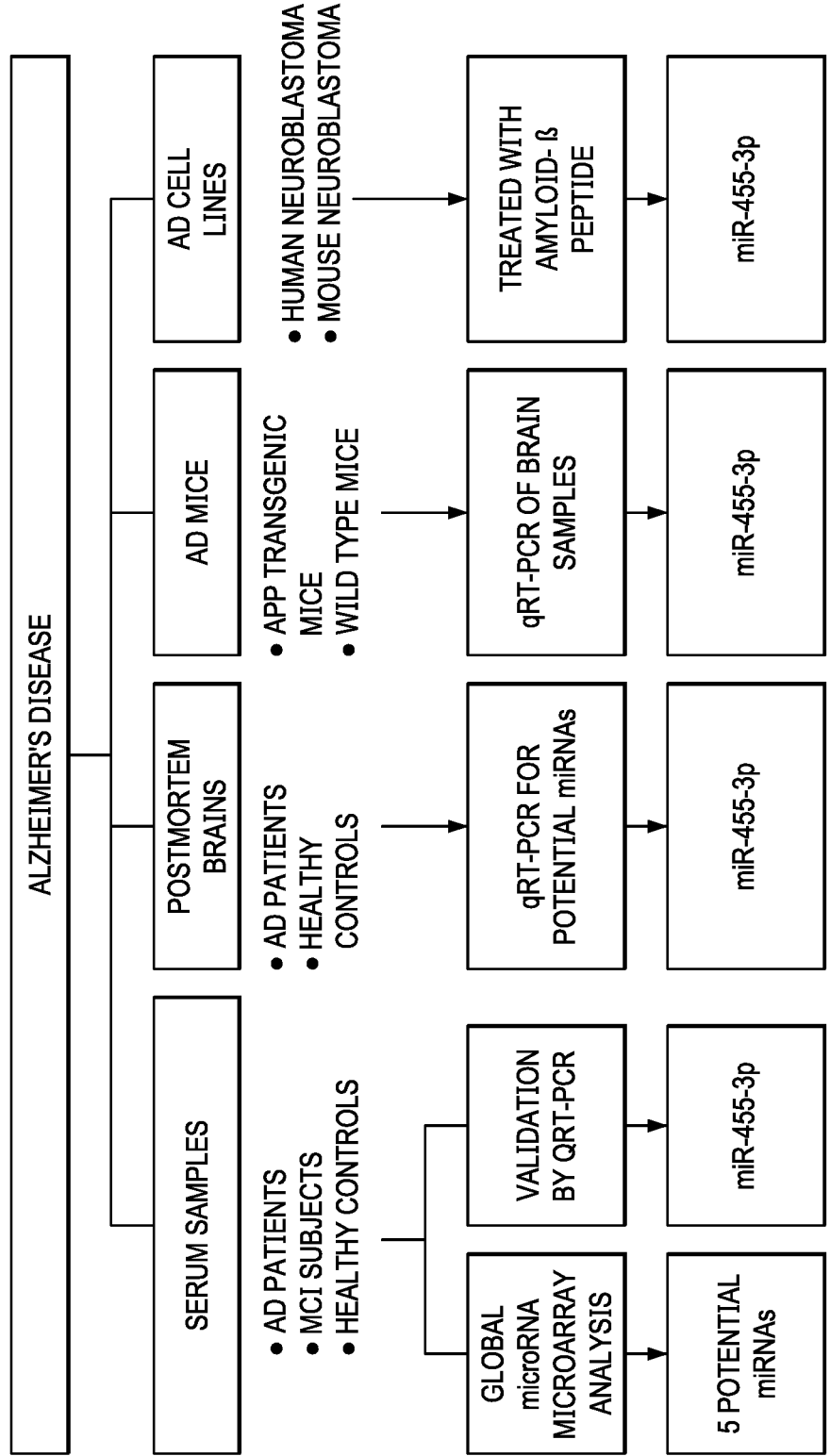
FIG. 8 shows MicroRNA 455-3p as a peripheral biomarker for Alzheimer's disease.

FIG. 8 shows MicroRNA 455-3p as a potential peripheral biomarker for Alzheimer's disease. To identify the early peripheral microRNA (miRNA) biomarkers for Alzheimer's disease (AD), the present inventors used different sources of materials in this study. Serum samples and postmortem brains from AD patients, brain tissues from AD transgenic mice and AD cell lines were used. Primary screening of serum samples from AD patients, MCI individuals and healthy subjects showed deregulated expression of five miRNAs by global Affymetrix based microarray analysis. MiRNAs were further validated in serum samples form AD patients, MCI individuals and healthy controls. Out of five, only miR-455-3p showed the most significant upregulation in AD and MCI cases compared to controls. Postmortem brains form AD patients also showed the significant upregulation of miR-455-3p in AD cases compared to controls. miR-455-3p expression also upregulated in the frontal cortices of APP transgenic mice compared to wild type mice. Finally, the inventors tested the miR-455-3p expression in human and mouse neuroblastoma cell lines treated with Amyloid-beta 42 peptide. In Amyloid-beta 42 treated cells, miR-455-3p expression was also elevated compared to control cells.

Figure 9:
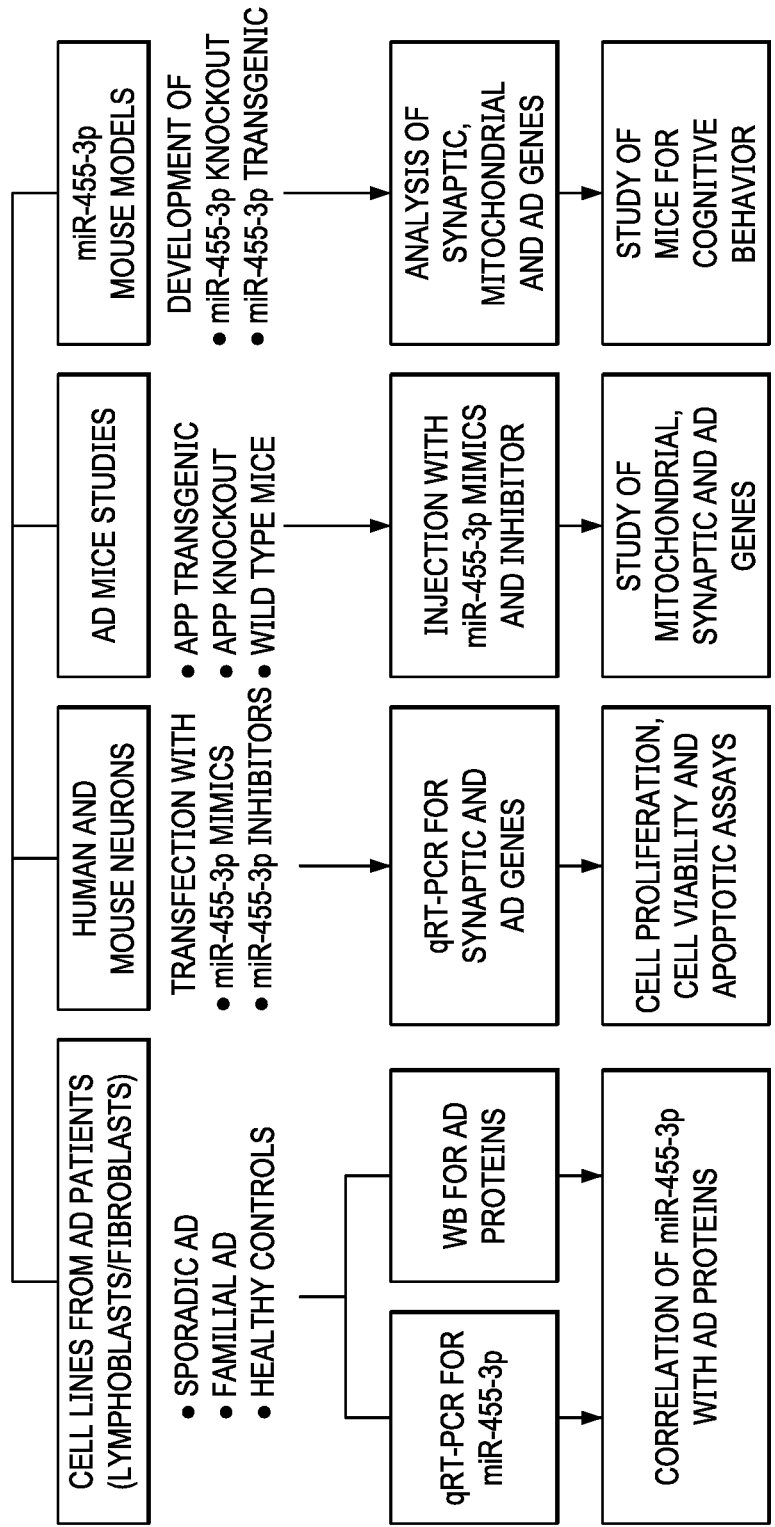
FIG. 9 shows the details of a microRNA 455-3p study.

FIG. 9 shows the details of a microRNA 455-3p study. Lymphoblasts and fibroblasts from AD patients and healthy controls (obtained from NIA cell line repositories) can be used in order to establish miR-455-3p as peripheral biomarker for Alzheimer's disease. Expression of miR-455-3p can be correlated with the levels of AD proteins. The molecular properties of miR-455-3p can also be used to mimic (overexpression) and (inhibitor) knockout approaches in human and mouse neuronal cells. These experiments can be used to determine the deleterious and protective effects of miR-455-3p in AD neurons. Using overexpression and/or knockouts of miR455-3p in APP transgenic and knockout mice it is possible to study the molecular features of miR455-3p during disease progression of AD. Finally, miR-455-3p transgenic and miR-455-3p knockout mice lines can be generated and used to explore the role of miR-455-3p in maintaining synaptic, mitochondrial and inflammatory functions and cognitive behavior.

In summary, the present inventors have identified multiple differentially expressed circulatory miRNAs in AD patients and subjects with MCI relative to healthy controls. A careful validation of differentially expressed miRNAs using AD postmortem brains, APP transgenic mice and AD cell lines revealed that miR-455-3p could be a potential diagnostic biomarker for AD. Further research is still needed to better understand the role of miR-455-3p in AD progression and pathogenesis.

Study subjects. Sera and DNA samples were collected from patients under the FRONTIERS project based at Garrison Institute on Aging (GIA), Texas Tech University Health Sciences Center (TTUHSC). These samples were obtained from 11 patients diagnosed with AD, 20 patients with MCI, and 18 healthy controls. The study protocol was approved by the Institutional Review Board for FRONTIERS, and all subjects provided informed written consent. All the bio-specimens were stored at GIA Bio-Bank. Patient information on demographic characteristics, medical history, biochemical profiles, and their risk factors for AD was gathered with a standardized questionnaire. Demographic and clinical characteristics of subjects are listed in the Table 3. After completing the questionnaire, all subjects underwent a detailed clinical examination to evaluate them for inclusion and exclusion criteria established by NINCDS-ADRDA. The inclusion criteria were: (1) 45 years and above age, (2) rural community based West Texas individuals, and (3) all study participants have assessed for cognitive functions. The exclusion criteria were: (1) individuals with strong medication and (2) too many health complications.

MiRNAs extraction. MiRNAs, including other small RNAs, were extracted from the serum samples with the miReasy serum/plasma kit (Qiagen, Germany) as per manufacturer's instructions (16). Briefly, 200 μl of serum samples were mixed with 5 volumes of a Qiazol lysis reagent and an equal volume of chloroform, and centrifuged to separate the aqueous phase. MiRNAs accumulated in the aqueous phase were precipitated with 100% ethanol. MiRNAs were washed with a buffer and 80% ethanol, and purified miRNAs were eluted in 15 μl of RNase-free water. RNA quality and quantity were measured by NanoDrop2000c (Thermo Scientific, USA).

Primary miRNAs screening by Affymetrix microarray. Detailed miRNAs screening of the serum samples were conducted in the University of Texas Southwestern Medical Center, Genomics and Microarray Core Facility, Dallas. The miRNA expression profiles were generated with Affymetrix GeneChip miRNA array v. 4.0 (Affymetrix). The GeneChip miRNA 2.0 arrays contain a 100% miRBase version 20 coverage: 30,424 mature miRNAs were from all organism; 5,214 from human, rat, and mouse miRNAs; and 1,996 from human snoRNA and scaRNA. It also provided 3,770 probe sets that are unique to human, mouse, and rat pre-miRNA hairpin sequences. The GeneChip miRNA 4.0 array demonstrated superior performance with 0.95 reproducibility (inter- and intra-lot) and >80% of transcripts were detected at 1.3 amol from 130 ng of total RNA. Data were represented by the GeneChip miRNA 4.0 array in 4 logs that correlated with a dynamic range of >0.97 signal and >0.94 fold-change.

Briefly, 8 μl of total RNA was treated for poly (A) tailing reaction at 37° C. for 15 min as per the protocol. 4 μl of 5× Flash Tag Biotin HSR ligation mix was added to poly (A) tailed RNA, and the mixture was incubated at 25° C. for 30 min, using the Flash Tag Biotin HSR Labeling kit following manufacturer's instructions (cat. no. HSR30FTA; Genisphere, LLC, Hatfield, Pa., USA). Biotin HSR that labeled with RNA was mixed with an array hybridization cocktail according to the GeneChip Eukaryotic Hybridization control kit manual and was processed using the Affymetrix GeneChip miRNA array. Samples were incubated on the hybridization array chip at 48° C. and 60 rpm for 16 to 18 hours. After hybridization, the chips were washed and stained by GeneChip hybridization, washed again, and then stained with an Affymetrix kit according to the manufacturer's protocols. The hybridized chips were scanned with an Affymetrix GCS 3000 7G Scanner (48).

Microarray data analysis. Raw data were obtained, using the Affymetrix GeneChip array in the form of an individual CHP file. Each sample was then analyzed, using Transcriptome Analysis Console software v. 3. Tukey's bi-weight average (log 2) intensity was analyzed with an ANOVA p-value (<0.05) and FDR p-value (<0.05) for all conditions, for all genes in the samples from AD, MCI and control group. SAM (significance analysis of microarray) with the R package was used to identify differentially expressed miRNA and gene probe sets in samples from the AD patients and the controls. Probe sets were considered biologically significant if the fold changes were 2 (49).

Validation of serum miRNAs expression using qRT-PCR. (i) Polyadenylation—One μg of total RNA was polyadenylated with an miRNA First-Strand cDNA synthesis kit (Agilent Technologies Inc., CA, USA), following manufacturer's instructions. Briefly, a polyA reaction was prepared by mixing RNA with 4.0 μl of 5× poly A polymerase buffer, 1.0 μl of rATP (10 mM), 1 μl of *E. coli* poly A polymerase, producing a final volume of 20 μl with RNase-free water. The tube with these components was incubated at 37° C. for 30 min, followed by another incubation at 95° C. for 5 min to terminate the adenylation reaction (50). (ii) cDNA synthesis –Ten μl of polyadenylated miRNAs were processed for cDNA synthesis with the miRNA First-Strand cDNA synthesis kit (Agilent Technologies Inc.). The following reaction components were combined in a tube: 2 μl of 10× AffinityScript RT buffer, 0.8 μl of dNTP mix (100 mM), 1 μl of RT adaptor primer (10 μM), 1.0 μl of AffinityScript RT/RNase Block enzyme, and polyadenylated RNA. The combination resulted in a reaction volume of 20 μl RNase-free water.

This reaction mixture was incubated at 55° C. for 5 min, then at 25° C. for 15 min, followed by an incubation at 42° C. for 30 min, and a final incubation at 95° C. for 5 min in a Veriti 96 well thermal cycler (Applied Biosystems, USA). Resulting cDNAs were diluted with 20 μl of RNase-free water and stored at 80° C. for further analysis. (iii) qRT-PCR for miRNAs—qRT-PCR reaction was performed by preparing a reaction mixture containing 1 μl of miRNA-specific forward primer (10 μm), 1 μl of a universal reverse primer (3.125 μm) (Agilent Technologies Inc., CA, USA), 10 μl of 2×SYBR® Green PCR master mix (Applied Biosystems, NY, USA), and 1 μl of cDNA. To this mixture RNase-free water was added up to a 20 μl final volume. Primers for hsa-miR-455-3p, miR-4674, miR-3613-3p, miR-4668-5p, and mir-6722 were synthesized commercially (Integrated DNA Technologies, Inc. Iowa USA) (Table 3).

TABLE 3 miRNAs primers sequences for qRT-PCR

| SEQ ID NO: | miRNA | Sequence (5' to 3') | Base pairs |
|---|---|---|---|
| 1 | Hsa-miR-455-3p | F-GCAGTCCATGGGCATATACAC | 21 |
| 2 | Mmu-miR-455-3p | F-GCAGTCCACGGGCATATACAC | 21 |
| 3 | Hsa-miR-4674-3p | F-CTGGGCTCGGGACGCGCGGCT | 21 |
| 4 | Hsa-miR-4668-5p | F-AGGGAAAAAAAAAAGGATTTGTC | 23 |
| 5 | Hsa-miR-3613-3p | F-ACAAAAAAAAAAGCCCAACCCTTC | 24 |
| 6 | Hsa-mir-6722 | F-GGCCTCAGGCAGGCGCACCCGA | 22 |
| 7 | | R-GGGTGGGCCAGGCTGTGGGCG | 22 |
| 8 | U6 snRNA | F-CGCTTCGGCAGCACATATACTAA | 23 |
| 9 | | R-TATGGAACGCTTCACGAATTTGC | 23 |
| 10 | snoRNA-202 | F-AGTACTTTTGAACCCTTTTCCA | 22 |

To normalize the miRNA expression, U6 snRNA (small nuclear RNA) expression was also quantified in the serum samples, which was used as an internal control. The reaction mixture of each sample was prepared in triplicates. The reaction was set in the 7900HT Fast Real Time PCR System (Applied Biosystems, USA) using following reaction conditions: initial denaturation at 95° C. for 5 min, denaturation at 95° C. for 10 sec, annealing at 60° C. for 15 sec, and extension at 72° C. for 25 sec. The relative levels of miRNAs in the AD patients versus the controls and versus the MCI subjects were determined in terms of their fold change, using the formula ($2^{-\Delta\Delta ct}$), where ΔCt was calculated by subtracting Ct of U6snRNA from the Ct of particular miRNAs, and ΔΔCt value was obtained by subtracting ΔCt of particular miRNAs in the controls from the ΔCt of miRNAs in the AD and MCI. qRT-PCR was performed in triplicate, and the data were expressed as the mean±SD (50,51).

Postmortem brains from AD patients. Postmortem brain tissues were obtained from the GIA Brain Bank. The frontal cortices of the postmortem brains were dissected from the AD patients (n=16) and controls (n=5). Demographic details of study participants were given in Table 4. The study protocol was approved by the Institute Ethical Committee at TTUHSC, and brain tissue was obtained after written informed consent from the deceased's relatives.

TABLE 4

Characteristics of postmortem brain tissues from controls and AD patients

| Cases | Gender | Age (yrs) | Braak Stage | PMI (hrs) | ApoE |
|---|---|---|---|---|---|
| HC1 | M | 71 | — | 9 | 3/4 |
| HC2 | M | 68 | — | 6.5 | 3/4 |
| HC3 | F | 72 | — | 11.5 | 3/3 |
| HC4 | F | 71 | — | 7.5 | 2/2 |
| HC5 | M | 82 | — | 6.25 | 3/3 |
| AD1 | M | 82 | IV | — | 3/4 |
| AD2 | M | 62 | IV | 5 | 3/3 |
| AD3 | M | 78 | IV | 7.5 | 3/4 |
| AD4 | M | 91 | IV | 8 | 3/3 |
| AD5 | F | 77 | V | 4 | 3/4 |
| AD6 | F | 86 | V | 3.5 | 3/4 |
| AD7 | F | 86 | V | 5 | 3/4 |
| AD8 | F | 75 | V | 4 | 3/4 |
| AD9 | F | 80 | V | 5 | 3/4 |
| AD10 | M | 78 | V | 7 | 3/4 |
| AD11 | M | 74 | VI | 7 | 3/4 |
| AD12 | F | 81 | VI | 6.25 | 3/3 |

TABLE 4-continued

Characteristics of postmortem brain tissues from controls and AD patients

| Cases | Gender | Age (yrs) | Braak Stage | PMI (hrs) | ApoE |
|---|---|---|---|---|---|
| AD13 | F | 83 | VI | 9.25 | 3/4 |
| AD14 | F | 86 | VI | 6 | 3/4 |
| AD15 | M | 84 | VI | 8 | 3/3 |
| AD16 | M | 82 | VI | 5.25 | 3/4 |

MiRNAs extraction and qRT-PCR. MiRNAs extraction and cDNA synthesis were followed as described above, while total RNA was isolated from the 80 mg of frontal cortices using the TriZol RT reagent (Ambion, USA) as per manufacturer instructions. Briefly, tissue samples were homogenized in 1 ml of TriZol reagent with Bio-Gen PRO200 Homogenizer (PRO Scientific Inc., CT, USA) in a 2-ml RNase-free tube. Chloroform (0.2 ml) was added to the tissue homogenate, vigorously shaken for 15 seconds, and stored for 5 min at room temperature. The mixture was then centrifuged at 12,000 g for 15 min at 4° C. The supernatant was transferred to a new tube and precipitated with 0.5 ml of isopropanol for 15 min at room temperature. Samples were centrifuged at 12,000 g for 10 min at 4° C. The resulting RNA pellet was washed with 1 ml of 75% ethanol and centrifuged at 7,500 g for 5 min at 4° C. The RNA pellet was dried and dissolved in 20 µl of DEPC-treated water. The quality and quantity of the RNA were analyzed by Nano-Drop analysis. The value of absorbance of each brain RNA sample ($A_{260}/A_{280}$) was 1.8 to 2.0. cDNA was synthesized from 1 µg of RNA using miRNA First-Strand cDNA synthesis kit (Agilent Technologies Inc.). qRT-PCR were analyzed for miR-455-3p, miR-4674, miR-3613-3p, miR-4668-5p, and mir-6722 as described previously.

Animal models. Amyloid-β transgenic (APP) mice were generated with the mutant human APP gene 695-amino-acid isoform and a double mutation ($Lys^{670}$ Asn and $Met^{671}$Leu) (35). The APP mouse model exhibits age-dependent Aβ plaques as well as a distribution of Aβ plaques in the cerebral cortex and the hippocampus, but not in the striatum, the deep gray nuclei, and the brain stem. Disease in this mouse model parallels AD in that elevated amounts of soluble Aβ correlate with increased free-radical production, and the Aβ plaques evoke a microglial reaction in their immediate vicinity. Cerebral cortex tissues were collected from 6-month-old APP transgenic mice (n=6) and age-matched, non-transgenic wild-type mice (n=6). To determine transgene-positive mice to model the human APP, genotyping was performed in accordance with the TTUHSC Policy on Genotype Tissue Collection, using the DNA prepared from tail biopsy and PCR amplification (35). All mice were observed daily by a veterinary caretaker and also examined twice weekly by laboratory staff. If any mice showed premature signs of neurological deterioration, they were euthanized before experimentation according to euthanasia procedure approved by the TTUHSC-IACUC and were not used in the study.

Amyloid-$β_{(1-42)}$ treatment to cell lines. Human neuroblastoma (SH-SY5Y) and mouse neuroblastoma (N2a) cell lines were purchased from American Tissue Type Collection (ATCC) (Virginia, USA). Cells were grown in a medium (1:1) Dulbecco's modified eagle's medium and minimum essential medium, 5% fetal bovine serum, 1× penicillin and streptomycin) at 37° C. in a humidified incubator with a 5% $CO_2$ environment. After the cells were seeded, they were allowed to grow for 24-48 hours or until 80% confluence in 6-well plates. They were then used for experimentation. Two different groups of cells were used: (1) untreated SH-SY5Y/N2a cells and (2) $Aβ_{(1-42)}$ peptide treated SH-SY5Y/N2a cells. They were incubated with the $Aβ_{(1-42)}$ peptide (20 mM final concentration) in triplicate for 6 hours. Both groups of cells were harvested after treatment and processed for total RNA extraction and miR-455-3p quantification.

MiRNAs pathway analysis. MiRNAs that were associated with signaling pathways were analyzed with the miRPath v3.0 web server algorithm (52). Briefly, species was defined as 'human, mouse' and miR-455-3p, miR-4674, miR-3613-3p, miR-4668-5p, and mir-6722 were entered. MiRNAs that target genes and biological pathways were analyzed, using microT-CDS and TarBase to classify the GO category, the P<0.05 of the KEGG pathway enrichment, and the microT-CDS threshold (0.8). The miRNA-targeted genes in different KEGG molecular pathways were ranked according to their P-value. The false discovery rate (FDR) P<0.05 was considered statistically significant.

Statistical analysis. The qRT-PCR validation analysis was based on the $2^{-ΔΔCT}$ value of genes in each sample from AD, MCI subjects and controls. Statistical analysis was performed with Prism software, v, 6 (La Zolla, Calif.). P-value was calculated, based on the paired and unpaired t-tests for analyzing 2 groups and using one-way comparative analysis of variance (ANOVA) when comparing between more than 2 groups. P<0.05 was considered statistically significant.

Example 2

The goal of present study was to identify a suitable, non-invasive, blood-based early biomarker for AD detection. To achieve this goal, the inventors focused on circulatory microRNAs (cmiRNAs), which are quite stable in peripheral circulation and levels of particular miRNA seems to be changing with disease severity. The previous research findings on human serum samples from AD patients, MCI individual and healthy subjects identified significant number of deregulated miRNAs in patients compared to controls (Kumar et al., 2017). A few of them were significantly upregulated and some were down regulated in AD and MCI individual compared to healthy controls. One of the most suitable identified candidate in the study was microRNA-455-3p. Expression of miR-455-3p was found to be significantly upregulated in AD serum samples, AD postmortem brains, AD mouse model, and AD cell lines (Kumar et al., 2017). Upregulation of miR-455-3p in different cell and mouse models of AD proven its biomarker potential for AD. To further strengthen the findings, the present study is focused on the AD postmortem brains obtained from NIH NeuroBioBanks, human fibroblast, and B-lymphocytes cell lines derived from familial AD and sporadic AD patients. Expression of miR-455-3p was quantified and its diagnostic potential was examined in different sources. Further, in-silico analysis was performed to understand the roles and downstream application of miR-455-3p in AD. Findings from this study, will provide the valuable information about miR-455-3p role in AD and in search of pre-clinical biomarker for early AD detection.

Study Subjects. (a) AD postmortem brains—Postmortem brains from AD patients and healthy controls were obtained from three NIH NeuroBioBanks—(1) Human Brain and Spinal Fluid Resource Center, 11301 Wilshire Blvd (127A), Los Angeles, Calif. (2) Brain Endowment Bank, University of Miami, Millar School of Medicine, 1951, NW 7th Avenue Suite 240, Miami, Fla. (3) Mount Sinai NIH Brain and Tissue Repository, 130 West Kingsbridge Road Bronx, N.Y. Brain tissues were dissected from the Brodmann's Area 10 of the frontal cortices from AD patients (n=27) and age and sex matched healthy controls (n=15). Demographic and clinical details of study specimens were given in Table 5.

(b) AD patients cell lines—Human skin fibroblast and Lymphoblast cell culture systems were used for these studies. Banked skin fibroblasts and lymphoblast cells with the diagnoses AD, non-AD dementia (e.g., Huntington's disease and Parkinson's disease, and schizophrenia), and age-matched control were obtained from the Coriell Institute of Medical Research, Camden, N.J., USA. The demographic details of cell lines along with their passage numbers, biopsy sources and tissue types were provided in Table 6. Cells were cultured and maintained in RPMI1640 for B-lymphocytes and MEM media for Fibroblasts (Life Technologies Corporation, NY, USA; supplemented with 10% Fetal Bovine Serum and 1× penicillin/streptomycin) at 37.0 with 5% $CO_2$ to the 90-100% confluence stage in 25 and 75 $cm^2$ cell culture flasks.

TABLE 5

Demographic and clinical details of the brain samples

| S. No | Sample ID | Age | Sex | Neuro pathology | Structure | Autolysis time |
|---|---|---|---|---|---|---|
| 1 | 4130 | 67 | F | Control | Broadmann's Area 10 | 11.8 |
| 2 | 4431 | 68 | F | Control | Broadmann's Area 10 | 23.7 |
| 3 | 4660 | 73 | F | Control | Broadmann's Area 10 | 18.5 |
| 4 | 5072 | 83 | M | Control | Broadmann's Area 10 | 19.5 |
| 5 | 5190 | 68 | M | Control | Broadmann's Area 10 | 20.3 |
| 6 | HCT15HAO1713 | 70 | M | Control | Broadmann's Area 10 | 12.7 |
| 7 | HCTZZC1711 | 82 | F | Control | Broadmann's Area 10 | 14.2 |
| 8 | HCT15HBC1709 | 83 | M | Control | Broadmann's Area 10 | 25 |
| 9 | HCTZZT1702 | 84 | M | Control | Broadmann's Area 10 | 15.5 |
| 10 | HCT15HBU1704 | 91 | F | Control | Broadmann's Area 10 | 18.7 |
| 11 | 77428 | 65 | M | Control | Broadmann's Area 10 | 3.8 |
| 12 | 77431 | 103 | F | Control | Broadmann's Area 10 | 3.8 |
| 13 | 77433 | 75 | M | Control | Broadmann's Area 10 | 5 |
| 14 | 77436 | 93 | M | Control | Broadmann's Area 10 | 4.1 |
| 15 | 77437 | 84 | F | Control | Broadmann's Area 10 | 5.4 |
| 16 | 4513 | 74 | M | AD | Broadmann's Area 10 | 15.6 |
| 17 | 4498 | 76 | M | AD | Broadmann's Area 10 | 12.9 |
| 18 | 4204 | 68 | M | AD | Broadmann's Area 10 | 11.9 |
| 19 | 4203 | 72 | F | AD | Broadmann's Area 10 | 20.3 |
| 20 | 4454 | 82 | F | AD | Broadmann's Area 10 | 9 |
| 21 | 4043 | 80 | F | AD | Broadmann's Area 10 | 13 |
| 22 | 4382 | 74 | F | AD | Broadmann's Area 10 | 16.2 |
| 23 | 4617 | 73 | F | AD | Broadmann's Area 10 | 18.9 |
| 24 | 4718 | 93 | F | AD | Broadmann's Area 10 | 8.2 |
| 25 | 4608 | 80 | M | AD | Broadmann's Area 10 | 3.1 |
| 26 | 4752 | 89 | M | AD | Broadmann's Area 10 | 9 |
| 27 | 4788 | 65 | M | AD | Broadmann's Area 10 | 7.8 |
| 28 | HBFR1703 | 69 | F | AD | Broadmann's Area 10 | 22 |
| 29 | HBFQ1711 | 77 | M | AD | Broadmann's Area 10 | 18 |
| 30 | HBJG1710 | 79 | M | AD | Broadmann's Area 10 | 23.8 |
| 31 | HBDA1704 | 80 | M | AD | Broadmann's Area 10 | 22.1 |
| 32 | HCTYN1713 | 80 | F | AD | Broadmann's Area 10 | 6.5 |
| 33 | HBDI1710 | 85 | F | AD | Broadmann's Area 10 | 8 |
| 34 | HBEM1701 | 86 | M | AD | Broadmann's Area 10 | 15.5 |
| 35 | HBIP1701 | 90 | F | AD | Broadmann's Area 10 | 22.1 |
| 36 | HBCG1703 | 90 | F | AD | Broadmann's Area 10 | 8.5 |
| 37 | HCTZX1702 | 95 | M | AD | Broadmann's Area 10 | 19.8 |
| 38 | 77423 | 79 | F | AD | Broadmann's Area 10 | 6.5 |
| 39 | 77424 | 69 | M | AD | Broadmann's Area 10 | 5.4 |
| 40 | 77425 | 75 | M | AD | Broadmann's Area 10 | 8 |
| 41 | 77426 | 94 | F | AD | Broadmann's Area 10 | 4.3 |
| 42 | 77427 | 82 | M | AD | Broadmann's Area 10 | 20.6 |

TABLE 6

Details of human Fibroblasts and B-lymphocytes

| S. No. | Catalog no | Passage no | Sex | Age (Years) | Biopsy sources | Tissue type | Race | Disease status |
|---|---|---|---|---|---|---|---|---|
| (A) Fibroblasts | | | | | | | | |
| 1 | AG02261 | 11 | M | 61 | Abdomen | Skin | Caucasian | Healthy control |
| 2 | AG16104 | 6 | F | 55 | Arm | Skin | Black | Healthy control |
| 3 | AG16086 | 6 | F | 67 | Arm | Skin | Other | Healthy control |
| 4 | AG12207 | 13 | M | 68 | Arm | Skin | NA | Healthy control |
| 5 | AG02258 | 6 | F | 46 | Lung | Lung | Caucasian | Healthy control |
| 6 | AG02262 | 4 | M | 61 | Lung | Lung | Caucasian | Healthy control |
| 7 | AG06561 | 5 | F | 16FW[#] | Sacrum | Skin | Caucasian | Healthy control |
| 8 | AG12211 | 11 | M | 54 | Lung | Lung | Caucasian | Healthy control |
| 9 | AG05810 | 11 | F | 79 | Arm | Skin | Caucasian | Familial AD |
| 10 | AG06844 | 12 | M | 59 | Arm | Skin | Caucasian | Familial AD |
| 11 | AG07613 | 16 | M | 66 | Arm | Skin | Caucasian | Familial AD |
| 12 | AG09908 | 14 | F | 81 | Arm | Skin | Caucasian | Familial AD |
| 13 | AG04400 | 19 | F | 61 | Skin | Skin | Caucasian | Sporadic AD |
| 14 | AG06263 | 11 | F | 67 | Arm | Skin | Caucasian | Sporadic AD |
| 15 | AG06264 | 7 | F | 62 | Arm | Skin | NA | Sporadic AD |
| 16 | AG07375 | 6 | M | 71 | Arm | Skin | Caucasian | Sporadic AD |
| 17 | AG08243 | 7 | M | 72 | Arm | Skin | Caucasian | Sporadic AD |
| 18 | AG11368 | 15 | M | 77 | Skin | Skin | Caucasian | Sporadic AD |
| (B) B-Lymphocytes | | | | | | | | |
| 1 | AG16639 | na | M | 77 | Peripheral vein | Blood | Caucasian | Healthy control |
| 2 | AG11684 | na | M | 82 | Peripheral vein | Blood | Caucasian | Healthy control |
| 3 | AG12034 | na | F | 80 | Peripheral vein | Blood | Caucasian | Healthy control |
| 4 | AG11716 | na | M | 98 | Peripheral vein | Blood | Caucasian | Healthy control |
| 5 | AG12032 | na | M | 84 | Peripheral vein | Blood | Caucasian | Healthy control |
| 6 | AG16804 | na | F | 90 | Peripheral vein | Blood | Caucasian | Healthy control |
| 7 | AG16927 | na | M | 85 | Peripheral vein | Blood | Caucasian | Healthy control |
| 8 | AG16973 | na | F | 80 | Peripheral vein | Blood | Caucasian | Healthy control |
| 9 | AG10673 | na | F | 85 | Peripheral vein | Blood | Black | Healthy control |
| 10 | AG16907 | na | F | 88 | Peripheral vein | Blood | Caucasian | Healthy control |
| 11 | AG08242 | na | M | 72 | Peripheral vein | Blood | Caucasian | Familial AD |
| 12 | AG09905 | na | M | 72 | Peripheral vein | Blood | Caucasian | Familial AD |
| 13 | AG09907 | na | F | 71 | Peripheral vein | Blood | Caucasian | Familial AD |
| 14 | AG11755 | na | F | 85 | Peripheral vein | Blood | Caucasian | Familial AD |
| 15 | AG11757 | na | F | 81 | Peripheral vein | Blood | Caucasian | Familial AD |
| 16 | AG11758 | na | M | 83 | Peripheral vein | Blood | Caucasian | Familial AD |
| 17 | AG06204 | na | M | 67 | Peripheral vein | Blood | Caucasian | Sporadic AD |
| 18 | AG06868 | na | F | 60 | Peripheral vein | Blood | Caucasian | Sporadic AD |
| 19 | AG11366 | na | M | 52 | Peripheral vein | Blood | Caucasian | Sporadic AD |
| 20 | AG17512 | na | M | 70 | Peripheral vein | Blood | African American | Sporadic AD |
| 21 | AG17529 | na | F | 86 | Peripheral vein | Blood | African American | Sporadic AD |
| 22 | AG17574 | na | F | 83 | Peripheral vein | Blood | African American | Sporadic AD | na* not available

Ethical Approval and Consent. The study was conducted at the Garrison Institute on Aging (GIA), Texas Tech University Health Sciences Center (TTUHSC), and study protocol was approved by the Institutional Review Board of TTUHSC, Lubbock, Tex. for the use of biospecimens in Project FRONTIER (IRB #: L06-028). Regarding postmortem brains and cell lines used in the current study—each of the NIH NeuroBioBanks mentioned above operated under their institution's IRB approval. As determined by the FDA Research Involving Human Subjects Committee, current study did not reach the definition of "Human Subject Research" at 45 CFR 46.102(f) and thus, 45 CFR Part 46 does not apply (Ferguson et al., 2017). Further, according to Office for Human Research Protections Guidelines biospecimens obtained by the researchers from NIGMS Human Genetic Cell Repository are not considered to be human subjects because conducting research with the samples does not involve an intervention or interaction with the individual and the samples do not contain identifiable private information (www.coriell.org).

RNA Extraction—Total RNA was isolated from the 80 mg of frontal cortices using the TriZol RT reagent (Ambion, USA) as per manufacturer instructions. Briefly, tissue samples were homogenized in 1 ml of TriZol reagent with Bio-Gen PRO200 Homogenizer (PRO Scientific Inc., CT, USA) in a 2-ml RNase-free tube. Chloroform (0.2 ml) was added to the tissue homogenate, vigorously shaken for 15 s, and stored for 5 min at room temperature. The mixture was then centrifuged at 12,000 g for 15 min at 4° C. The supernatant was transferred to a new tube and precipitated with 0.5 ml of isopropanol for 15 min at room temperature. Samples were centrifuged at 12,000 g for 10 min at 4° C. The resulting RNA pellet was washed with 1 ml of 75% ethanol and centrifuged at 7,500 g for 5 min at 4° C. The RNA pellet was dried and dissolved in 50 µl of DEPC-treated water. The quality and quantity of the RNA were analyzed by NanoDrop analysis. The value of absorbance of each brain RNA sample (A260/A280) was Qualification of miRNAs Expression by Quantitative Real-Time PCR—Quantification Involved Three Steps:

Polyadenylation—One microgram of total RNA was polyadenylated with an miRNA First-Strand cDNA synthesis kit (Agilent Technologies Inc., CA, USA), following manufacturer's instructions. Briefly, a polyA reaction was prepared by mixing RNA with 4.0 µl of 5× poly A polymerase buffer, 1.0 µl of rATP (10 mM), 1 µl of E. coli poly A polymerase, producing a final volume of 20 µl with RNase free water. The tube with these components was incubated at 37° C. for 30 min, followed another incubation at 95° C. for 5 min to terminate the adenylation reaction (Kumar et al., 2014).

cDNA synthesis—Ten microliters of polyadenylated miRNAs were processed for cDNA synthesis with the miRNA First-Strand cDNA synthesis kit (Agilent Technologies Inc.). The following reaction components were combined in a tube: 2 µl of 10× AffinityScript RT buffer, 0.8 µl of dNTP mix (100 mM), 1 µl of RT adaptor primer (10 µM), 1.0 µl of AffinityScript RT/RNase Block enzyme, and polyadenylated RNA. The combination resulted in a reaction volume of 20 µl RNase-free water. This reaction mixture was incubated at 55° C. for 5 min, then at 25° C. for 15 min, followed by an incubation at 42° C. for 30 min, and a final incubation at 95° C. for 5 min in a Veriti 96 well thermal cycler (Applied Biosystems, USA). Resulting cDNAs were diluted with 20 µl of RNase-free water and stored at 80.0 for further analysis.

Real-time RT-PCR—Real-time RT-PCR reaction was performed by preparing a reaction mixture containing 1 µl of miRNA-specific forward primer (10 µm), 1 µl of a universal reverse primer (3.125 µm) (Agilent Technologies Inc., CA, USA), 10 µl of 2×SYBR Green PCR master mix (Applied Biosystems, NY, USA), and 1 µl of cDNA. To this mixture RNase-free water was added up to a 20 µl final volume. Primers for hsamiR-455-3p (Forward: 5' GCAGTC-CATGGGCATATACAC-3' (SEQ ID NO: 1), and U6snRNA (P1: 5'-GCTTCGGCAGCACATATACTAA-3' (SEQ ID NO: 8) and Reverse: 5'-TATGGAACGCTTCACGAAT-TTGC-3' (SEQ ID NO: 9)) were synthesized commercially (Integrated DNA Technologies, Inc. Iowa USA). To normalize the miRNA expression, U6 snRNA (small nuclear RNA) expression was also quantified in the tissue and cells, which was used as an internal control. The reaction mixture of each sample was prepared in triplicates. The reaction was set in the 7900HT Fast Real Time PCR System (Applied Biosystems, USA) using following reaction conditions: initial denaturation at 95° C. for 5 min, denaturation at 95° C. for 10 s, annealing at 60° C. for 15 s, and extension at 72° C. for 25 s. The relative levels of miR-455-3p in the AD patients vs. the controls subjects were determined in terms of their fold change, using the formula (2-11Ct), where 1Ct was calculated by subtracting Ct of U6snRNA from the Ct of miR-455-3p. Real-time RT-PCR was performed in triplicate, and the data were expressed as the mean±SD (Kumar et al., 2014; Hamam et al., 2016).

In-Silico Analysis for miR-455-3p. MiR-455-3p target genes were analyzed using various on-line miRNA algorithms (diana-microt, microrna.org, mirdb, rna22-has, targetminer, and targetscan-vert). Details about predictive and validated transcripts were obtained by searching hsamiR-455-3p.1 and hsa-miR-455-3p.2 isoforms. Target genes were checked for following parameters: (i) their representative transcripts, (ii) number of 3P-seq tags supporting UTR+5, (iii) link to sites in UTRs, (iv) conserved sites/poorly conserved sites, (v) cumulative weighted context++ score, (vi) total context++ score, and (vii) aggregate PCT (preferentially conserved targeting) values. Further, Predicted consequential pairing showed the miRNA-target complementarity at inside or outside the seed regions of miRNAs was checked at untranslated regions links (http://www.targetscan.org).

Statistical Analysis. The real-time RT-PCR data was analyzed by using the formula $2^{-\Delta CT}$ value of genes in each sample from AD patient's samples and controls. Statistical analysis was performed with Prism software, v, 6 (La Zolla, Calif.). P-value was calculated, based on the unpaired t-tests for analyzing two groups and using one way comparative analysis of variance (ANOVA) when comparing between more than two groups. ROC curve was plotted based on the 1CT value of samples in patients and control groups. Correlation analysis was performed using two tailed Pearson correlation coefficient (r) calculation considering 95% confidence interval. P<0.05 was considered statistically significant.

Up Regulation of miR-455-3p Expression in AD. AD Postmortem Brains—Total RNA was extracted from the postmortem brains of healthy controls (n=15) and AD patients (n=27) and expression of hsa-miR-455-3p was quantified by real-time RT-PCR analysis. Fold-change was calculated based on the 1CT value of miR-455-3p in AD patients' vs. healthy controls. The (ΔCT) value (mean±SD) was significantly (P=0.0001) higher in AD patients (−6.89±0.21) compared to the healthy controls (−8.94±0.56; FIG. 10A). Interestingly, fold-change analysis indicated the significantly higher expression of miR-455-3p in AD patients.

AD Fibroblasts—Similarly, expression of miR-455-3p was quantified in the skin fibroblast cells generated form familial AD patients (n=4), sporadic AD patients (n=6), and healthy control subjects (n=8). Differences in ΔCT values was evaluated among three groups using one-way ANOVA. Results showed the higher (−ΔCT) values (mean±SD) of miR-455-3p in familial and sporadic patients compared to controls. However, significant difference (P=0.014) in (−ΔCT) value was observed in sporadic cases (−7.35±1.39) compared to control samples (−9.37±0.76; FIG. 10B). AD B-Lymphocytes—Further, the inventors checked the level of miR-455-3p in B-lymphocytes obtained from familial AD patients (n=6), sporadic AD patients (n=6), and healthy controls (n=10). The (-ΔCT) (mean±SD) value was compared among three group using one-way ANOVA. Analysis showed the variations in miR-455-3p level among these groups, however significant difference (P=0.044) in (-ΔCT) value was reported between sporadic AD cases (−13.98±0.73) and controls (−15.50±0.80; FIG. 10C). Hence, results obtained from AD postmortem brains, AD fibroblast, and AD B-lymphocyte were conclusively confirmed the decisive role of miR-455-3p in AD assessment.

Receiver Operating Characteristics Curve Analysis of miR-455-3p. AD Postmortem Brains—To determine the diagnostic performance of miR-455-3p expression in AD patients, ROC curve was plotted using (ΔCT) values of miR-455-3p in AD patients and healthy controls. Analysis showed the significant area under ROC curve (AUROC) value of miR-455-3p (AUROC=0.792) with the 95% confidence interval was 0.637-0.948 (P=0.0018). The cut-off value was 8.16 with sensitivity of 88.89% (95% confidence interval: 70.84-97.65%) and specificity was 66.67% confidence interval: 38.38-88.18%) in AD brain samples compared with healthy controls (FIG. 11A).

In AD Fibroblasts—ROC curve was analyzed for miR-455-3p expression in fibroblast cells form familial and sporadic AD patients vs. healthy controls. However, significant AUC value was obtained for ROC curve when comparing between sporadic AD patients with healthy controls. AUROC value was (0.861) with 95% confidence interval of 0.6036-1.119 (P=0.037). The cut-off value was 9.12 with sensitivity of 83.33% (95% confidence interval: 35.88-99.58%) and specificity was also 66.67% with confidence interval (22.28-95.67%; FIG. 11B).

In AD B-Lymphocytes—Similarly ROC curve for miR-455-3p was analyzed in B-lymphocytes of AD patients. Analysis between sporadic AD patients and healthy controls showed the fair AUROC value (0.722) with 95% confidence interval of 0.4185-1.026 (P=0.20). The cut-off value was 14.90 with sensitivity of 66.67% (95% confidence interval: 22.28-95.67%) and specificity was 50.00% (95% confidence interval: 11.81-88.19%; FIG. 11C). Thus, analysis showed that ROC analysis of miR-455-3p in B-lymphocytes was not significant. However, data from postmortem AD brains and AD fibroblasts cells showed significant ROC curve data further confirmed that the miR-455-3p as a valuable molecule capable of discriminating the patients with AD from healthy individuals.

Figure 12A:
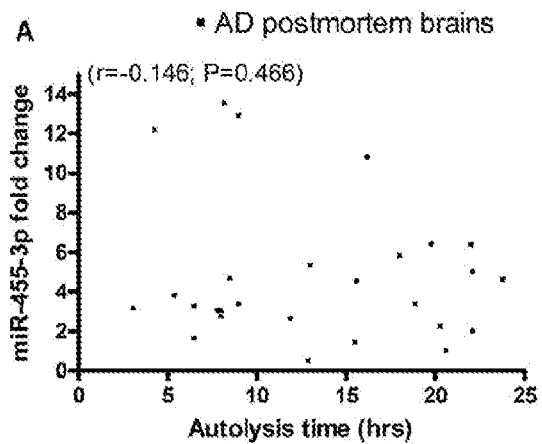
FIGS. 12A to 12D show scattered plot diagrams showing the Pearson correlation coefficient (r) values of miR-455-3p expression with (FIG. 12A) AD postmortem brains autolysis time (FIG. 12B) Age of AD postmortem brains (FIG. 12C) Age of AD fibroblast cells and (FIG. 12D) Age of AD B-lymphocytes.
Figure 12B:
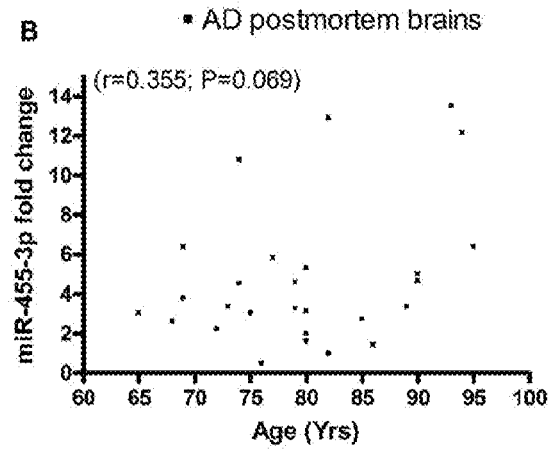
Figure 12C:
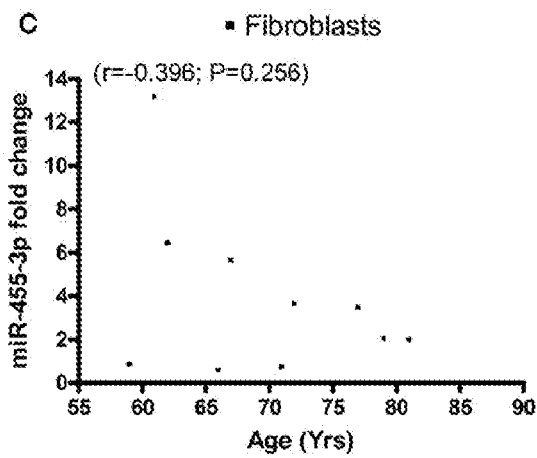
Figure 12D:
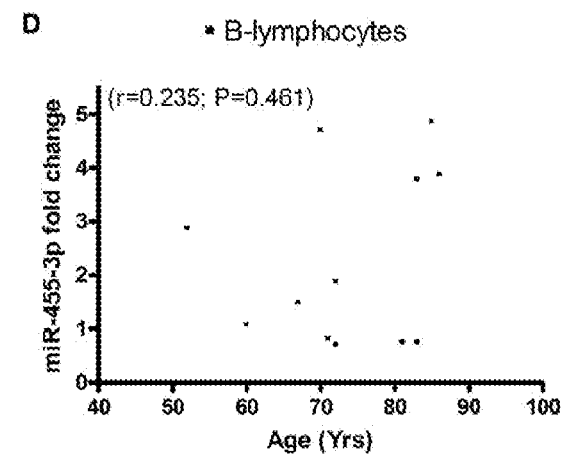

Correlation of miR-455-3p Expression with Patients' Demographic Data. The inventors analyzed miR-455-3p expression levels in relation to (1) postmortem interval, (2) AD patients' age, and also (3) donors' age of fibroblasts, and (4) B-lymphocytes using Pearson correlation coefficients (r). AD postmortem brains showed a negative correlation r=−0.146 (with 95% confidence interval: −0.498 to 0.247; P=0.466) between brains postmortem interval and miR-455-3p expression level (FIG. 12A). Whereas a positive correlation r=0.355 (with 95% confidence interval: −0.029 to 0.647; P=0.069) was observed between the age of AD postmortem brains and miR-455-3p level (FIG. 12B). However, P-values were not significant in both cases. Thus, results showed a trend of reduced levels of miR-455-3p with increased postmortem interval and increased trend of miR-455-3p with patients' age. As shown in FIGS. FIG. 12C, FIG. 12D, donors' age for fibroblasts (r=−0.396, 95% confidence interval: −0.821 to 0.310; P=0.256), and B-lymphocytes (r=0.235, 95% confidence interval: −0.391 to 0.713; P=0.461), the inventors did not find statistical significance, between donors age with miR-455-3p levels for fibroblasts and B-lymphocytes, indicating that donors age do not affect miR-455-3p expression levels.

In-Silico Analysis for miR-455-3p Function in AD. In-silico analysis was performed to understand the functions of miR-455-3p and its possible role in AD pathogenesis. Analysis was performed using the various bio-informatics algorithms such as DIANA-MICROT, MICRORNA.ORG, MIRDB, RNA22-HAS, TARGETMINER, and TARGETS-CAN-VERT. As per miRbase database, a total of 3,102 reads of miR-455-3p has been detected by deep sequencing in 62 experiments (www.mirbase.org). Each algorithm was run for miR-455-3p and validated/predictive target genes were analyzed. A total of 323 predicted transcripts/human genes were identified with conserved miR-455-3p.2 binding site. Out of these genes most potential 13 targets genes were screened for those were having the roles in AD pathogenesis. Important ones were: APP, NGF, USP25, PDRG1, SMAD4, UBQLN1, SMAD2, TP73, HSPBAP1, and NRXN1 (Table 7). miR-455-3p having at least one or two binding site at 3'UTR of the genes and total context++ score ranges from −0.1 to −0.46. For e.g., miR-455-3p binds at the two sequence sites of 3' UTR of APP gene at sequence position 522-528 and 3,139-3,145. Interaction of miR-455-3p at these sites will influence the expression level of APP genes. Hence, these analyses indicated the possible way the miR-455-3p involved in AD pathogenesis.

TABLE 7

Predictive/validated gene targets of miR-455-3p involved in AD

| S.No | Representative miRNA | Ortholog of target gene | Representative transcript | Gene name | 3P-seq tags + 5 | Conserved sites total | Cumulative weighted context ++ score | Total context ++ score | Aggregate PCT |
|---|---|---|---|---|---|---|---|---|---|
| 1 | hsa-miR-455-3p.2 | NGF | ENST00000369512.2 | nerve growth factor (beta polypeptide) | 27 | 1 | −0.46 | −0.46 | 0.38 |
| 2 | hsa-miR-455-3p.2 | USP25 | ENST00000285681.2 | ubiquitin specific peptidase 25 | 2012 | 2 | −0.45 | −0.45 | 0.6 |
| 3 | hsa-miR-455-3p.2 | PDRG1 | ENST00000202017.4 | p53 and DNA-damage regulated 1 | 116 | 1 | −0.45 | −0.45 | <0.1 |
| 4 | hsa-miR-455-3p.2 | SMAD4 | ENST00000398417.2 | SMAD family member 4 | 403 | 2 | −0.3 | −0.32 | <0.1 |
| 5 | hsa-miR-455-3p.2 | UBQLN1 | ENST00000376395.4 | ubiquilin 1 | 471 | 2 | −0.3 | −0.33 | <0.1 |

TABLE 7-continued

Predictive/validated gene targets of miR-455-3p involved in AD

| S.No | Representative miRNA | Ortholog of target gene | Representative transcript | Gene name | 3P-seq tags + 5 | Conserved sites total | Cumulative weighted context ++ score | Total context ++ score | Aggregate PCT |
|---|---|---|---|---|---|---|---|---|---|
| 6 | hsa-miR-455-3p.2 | APP | ENST00000346798.3 | amyloid beta (A4) precursor protein | 4570 | 2 | −0.29 | −0.35 | <0.1 |
| 7 | hsa-miR-455-3p.1 | SMAD2 | ENST00000262160.6 | SMAD family member 2 | 1196 | 2 | −0.2 | −0.28 | 0.33 |
| 8 | hsa-miR-455-3p.1 | TP73 | ENST00000378280.1 | tumor protein p73 | 831 | 1 | −0.14 | −0.14 | 0.3 |
| 9 | hsa-miR-455-3p.1 | VAMP2 | ENST00000316509.6 | vesicle-associated membrane protein 2 (synaptobrevin 2) | 1840 | 1 | −0.11 | −0.11 | 0.26 |
| 10 | hsa-miR-455-3p.1 | HSPBAP1 | ENST00000383659.1 | HSPB (heat shock 27 kDa) associated protein 1 | 22 | 1 | −0.11 | −0.15 | <0.1 |
| 11 | hsa-miR-455-3p.1 | NRXN1 | ENST00000342183.5 | neurexin 1 | 5 | 1 | −0.1 | −0.1 | 0.3 |

The purpose of the study was to determine the blood based peripheral biomarkers for AD. The inventors recently conducted a high throughput microRNA analysis using serum-derived RNA samples from MCI subjects, AD patients, and healthy control subjects (Kumar et al., 2017). The inventors found several differentially expressed miRNAs in MCI subjects and patients with AD relative to healthy controls. Further, the inventors verified differentially expressed miRNAs using real-time RT-PCR from serum-derived miRNAs, and also from cell and mouse models of AD. In the current study, the inventors extended the investigations using large numbers of fibroblasts, B-lymphocytes from familial and sporadic AD patients and age-matched control subjects. The inventors found miR-455-3p levels were upregulated in the fibroblasts and B-lymphocytes from AD patients relative to healthy control subjects. However, a significant difference was observed in the cells form sporadic AD patients compared to healthy controls. Similarly, in B-lymphocytes, miR-455-3p level was significantly upregulated in sporadic AD cases compared to controls (P=0.044). Receiver operating characteristic curve analysis indicated the significant area under curve value of miR-455-3p in AD postmortem brains (AUROC=0.792; P=0.001) and AD fibroblasts cells (AUROC=0.861; P=0.03). These observations show that miR-455-3p is a biomarker for sporadic AD.

An early stage pre-clinical diagnostic biomarkers are urgently needed to detect disease process early on in life and take necessary action to prevent and/or delay disease progression. Recent molecular biology studies using serum/plasma revealed that several circulatory microRNAs can be used as potential peripheral biomarkers for AD (Kumar and Reddy, 2016). However, these circulatory microRNAs are needed further validation using postmortem AD brains and cell and mouse models of AD. Therefore, more accurate and mechanistic research is needed to determine potential candidates as biomarkers for AD. As mentioned above, the recent lab study on AD serum samples and other AD sources/AD mouse model unveiled the miR-455-3p as potential biomarker candidate for AD. Many other reports identified the role of miR-455-3p in several cancers and chondrogenic differentiation (Chen et al., 2016; Cheng et al., 2016; Li et al., 2016; Liu et al., 2016; Qin et al., 2016; Zheng et al., 2016; Zhao et al., 2017). The study was the first to reveal the higher expression level of miR-455-3p in persons with AD.

Current study is the continuation of the ongoing biomarkers research project in the Reddy Lab. Here, first the inventors investigated miR455-3p levels in the well-defined postmortem brain tissues from AD patients. All tissues were dissected from the affected area (Broadmann's area 10) of AD patients and commonly used for the investigation of AD pathogenesis (Wilcock et al., 2015; De Rossi et al., 2016; Shackleton et al., 2017). The current study on AD postmortem findings revealed that miR-455-3p levels are significantly increased in a large number (n=27) of AD brains and a significant AUC value also strengthen its biomarker potential. However, the inventors don't know the exact reason for the upregulation of miR-455-3p in AD brains and further, the inventors still do not know molecular mechanism(s) of its increased levels. By way of explanation, and in no way a limitation of the present invention, and eased on current the upregulation of miR-455-3p—may be a compensatory to the amyloid beta toxicity in disease process.

Beside brain tissues, the inventors also investigated the AD fibroblasts and B-lymphocytes for miR-455-3p expression. These AD cell lines are the good sources for the investigation of AD pathologies and associated molecular changes in the patients' genome (Khan and Alkon, 2016). Both cell types showed the significantly higher levels of miR-455-3p, especially in sporadic AD cases but not in familial AD. Further, high level of miR-455-3p in AD fibroblasts and lymphoblasts indicate that increased levels of miR-455-3p is a typical feature of AD-both in the brain and peripheral cells. Alteration of miR-455-3p expression in AD cell lines indicates the strong molecular association of miR-455-3p with AD progression.

In order to expose the roles and functions of miR-455-3p in AD, in-silico analysis provides the valuable information. As described 11 genes were reported to involve in AD progression (FIG. 3) (Burton et al., 2002; Li et al., 2004; Slifer et al., 2006; Toth et al., 2013; Sindi et al., 2014; Jung et al., 2015, 2016; Malkki, 2015; Vallortigara et al., 2016; Kuruva et al., 2017). To understand the roles of miR-455-3p in AD, expression of these genes needs to be studied by using miR-455-3p modulation approaches (mimics/inhibitors). In this direction, next phase of the study is to determine the effect of miR-455-3p on its AD related target genes. Current focus of the laboratory is to understand the role of miR-455-3p in APP processing and amyloid beta modulation, using miR-455-3p mimics and inhibitor treatments. The inventors also predict that two potential binding sites of miR-455-3p at the 3'UTR of APP gene may be involved in the modulation of full length APP. Further, the inventors also predict that miR-455-3p affects the APP processing and amyloid beta production.

In summary, for the first time, the inventors report that microRNA455-3p is a peripheral biomarker for AD. These findings are based on (1) blood-based circulatory microRNAs from AD patients, (2) AD postmortem brains, AD cell lines, and AD mouse models and a large number of AD fibroblasts and lymphoblasts.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Example 1

1. Lukiw J (2013) Circular RNA (circRNA) in Alzheimer's Disease (AD). Frontiers in Genetics 4:307.
2. Reddy P H, et al. (2017) A critical evaluation of neuroprotective and neurodegenerative MicroRNAs in Alzheimer's disease. Biochem Biophys Res Commun 483(4):1156-1165.
3. LaFerla F M, Green K N, Oddo S (2007) Intracellular amyloid-β in Alzheimer's disease. Nat Rev Neuro 8(7): 449-509.
4. Mattson M P (2004) Pathways towards and away from Alzheimer's disease. Nature 430(7000):631-639.
5. Reddy P H, et al. (2010) Amyloid-β and mitochondria in aging and Alzheimer's disease: Implications for synaptic damage and cognitive decline. J Alz Dis 20(2010):S499-S512.
6. Kumar P, et al. (2013) Circulating miRNA biomarkers for Alzheimer's disease. Plos One 8(7):e69807.

7. Zafari S, et al. (2015) Circulating biomarkers panels in Alzheimer's disease. Gerontology 61(6):497-503.
8. Zhao Y, et al. (2015) microRNA-based biomarkers and the diagnosis of Alzheimer's disease. Frontiers in Neurology 6:162.
9. Bartel D P (2007) MicroRNAs: Genomics, Biogenesis, Mechanism and Function. Cell 116(2):281-297.
10. Adlakha Y K, Saini N (2014) Brain microRNAs and insights into biological functions and therapeutic potential of brain enriched miRNA-128. Mol Cancer 13:33.
11. Kumar S, Reddy P H (2016) Are circulating microRNAs peripheral biomarkers for Alzheimer's disease? Biochim Biophys Acta 1862(9):1617-1627.
12. Ha M, Kim V N (2015) Regulation of microRNA biogenesis. Nat Rev Mol Cell Biol 15(8):509-524.
13. Boon R A, Vickers K C (2007) Intercellular Transport of MicroRNAs. Arterioscler Thromb Vasc Biol 33(2)186-192.
14. Schipper H M, et al. (2007) microRNA expression in Alzheimer blood mononuclear cells. Gene Regul Syst Biol 20(1):263-274.
15. Alexandrov P N, et al. (2012) microRNA (miRNA) speciation in Alzheimer's disease (AD) cerebrospinal fluid (CSF) and extracellular fluid (ECF). Int J Biochem Mol Biol 3(4)365-373.
16. Geekiyanage H, et al. (2012) Blood serum miRNA: Non-invasive biomarkers for Alzheimer's disease. Exp Neurol 235(2):491-496.
17. Cheng L, et al. (2015) Prognostic serum miRNA biomarker associated with Alzheimer's disease shows concordance with neuropsychological and neuroimaging assessment. Mol Psychiatry 20 (10):1188-1196.
18. Galimberti D, et al. (2014) Circulating miRNAs as potential biomarkers in Alzheimer's disease. J Alz Dis 42(4):1261-1267.
19. Tan L, et al. (2014) Circulating miR-125 as a biomarker of Alzheimer's disease. J Neurol Sci 336(1-2):52-56.
20. Satoh J, Kino Y, Niida S (2015) MicroRNA-Seq data analysis pipeline to identify blood biomarkers for Alzheimer's disease from public data. Biomarker Insights 10:21-31.
21. Dong H, et al. (2015) Serum microRNA profiles serve as novel biomarkers for the diagnosis of Alzheimer's disease. Dis. Markers (2015):625659.
22. Williams J, et al. (2016) Are microRNAs true sensors of ageing and cellular senescence?. Ageing Res Rev S1568-1637(16):30168-30164.
23. Wu H Z Y, et al. (2016) Circulating microRNAs as biomarkers of Alzheimer's disease: A systemic review. J Alz Dis 49(3):755-766.
24. Liu C C, et al. (2013) Apolipoprotein E and Alzheimer disease: risk, mechanisms and therapy. Nat Rev Neurol 9(2):106-118.
25. Zheng J, et al. (2016) MicroRNA-455-3p Inhibits Tumor Cell Proliferation and Induces Apoptosis in HCT116 Human Colon Cancer Cells. Med Sci Monit 22:4431-4437.
26. Zhang Z, et al. (2015) MiR-455-3p regulates early chondrogenic differentiation via inhibiting Runx2. FEBS Lett 589(23):3671-3678.
27. Chen W, et al. (2016) MicroRNA-455-3p modulates cartilage development and degeneration through modification of histone H3 acetylation. Biochim Biophys Acta 1863(12):2881-2891.
28. Lalevée S, Lapaire O, Bühler M (2014) miR455 is linked to hypoxia signaling and is deregulated in preeclampsia. Cell Death Dis 5:e1408.
29. Zhang H, et al. (2015) MicroRNA-455 regulates brown adipogenesis via a novel HIF1an-AMPK-PGC1α signaling network. EMBO Rep 16(10):1378-1393.
30. Freischmidt A, et al. (2014) Serum microRNAs in patients with genetic amyotrophic lateral sclerosis and pre-manifest mutation carriers. Brain 137(Pt 11):2938-2950.
31. Wang N, et al. (2015) Profiling and initial validation of urinary microRNAs as biomarkers in IgA nephropathy. PeerJ 3:e990.
32. Yan S, et al. (2017) Altered microRNA profiles in plasma exosomes from mesial temporal lobe epilepsy with hippocampal sclerosis. Oncotarget 8(3):4136-4146.
33. Lugli G, et al. (2015) Plasma Exosomal miRNAs in Persons with and without Alzheimer Disease: Altered Expression and Prospects for Biomarkers. PLoS One 10(10):e0139233.
34. Knyazev E N, et al. (2016) MicroRNA hsa-miR-4674 in Hemolysis-Free Blood Plasma Is Associated with Distant Metastases of Prostatic Cancer. Bull Exp Biol Med 161 (1):112-115.
35. Hsiao K, et al. (1996) Correlative memory deficits, Abeta elevation, and amyloid plaques in transgenic mice. Science 274(5284):99-102.
36. Manczak M, et al. (2016) Protective effects of reduced dynamin-related protein 1 against amyloid beta-induced mitochondrial dysfunction and synaptic damage in Alzheimer's disease. Hum Mol Genet 25(22):4881-4897.
37. Swingler T E, et al. (2012) The expression and function of microRNAs in chondrogenesis and osteoarthritis. Arthritis Rheum 64(6):1909-1919.
38. Das P, Golde T (2006) Dysfunction of TGF-beta signaling in Alzheimer's disease. J Clin Invest 116(11):2855-2857.
39. von Bernhardi R, et al. (2015) Role of TGFβ signaling in the pathogenesis of Alzheimer's disease. Front Cell Neurosci 9:426.
40. Ferrer I, Blanco R (2000) N-myc and c-myc expression in Alzheimer disease, Huntington disease and Parkinson disease. Brain Res Mol Brain Res. 77(2):270-276.
41. Rosenmann H, et al. (2004) An association study of a polymorphism in the heparin sulfate proteoglycan gene (perlecan, HSPG2) and Alzheimer's disease. Am J Med Genet B Neuropsychiatr Genet 128B(1):123-125.
42. Lee H G, et al. (2006) Ectopic expression of phospho-Smad2 in Alzheimer's disease: uncoupling of the transforming growth factor-beta pathway?. J Neurosci Res 84(8):1856-1861.
43. Lee H G, et al. (2009) The neuronal expression of MYC causes a neurodegenerative phenotype in a novel transgenic mouse. Am J Pathol 174(3):891-897.
44. Cheng J S, et al. (2009) Collagen VI protects neurons against Abeta toxicity. Nat Neurosci 12(2):119-121.
45. Donovan L E, et al. (2013) Exploring the potential of the platelet membrane proteome as a source of peripheral biomarkers for Alzheimer's disease. Alzheimers Res Ther 5(3):32.
46. Xie K, et al. (2013) Tenascin-C deficiency ameliorates Alzheimer's disease-related pathology in mice. Neurobiol Aging 34(10):2389-2398.
47. Mastroeni D, et al. (2013) Reduced RAN expression and disrupted transport between cytoplasm and nucleus; a key event in Alzheimer's disease pathophysiology. PLoS One 8(1):e53349.

48. Godfrey A C, et al. (2013) Serum microRNA expression as an early marker for breast cancer risk in prospectively collected samples from the Sister Study cohort. Breast Cancer Res 15(3):R42.

49. Shi W L, et al. (2016) Integrated miRNA and mRNA expression profiling in fetal hippocampus with Downsyndrome. J Biomed Sci 23(1):48.

50. Kumar S, et al. (2014) Severity of hepatitis C virus (genotype-3) infection positively correlates with circulating microRNA-122 in patients sera. Dis Markers (2014): 435476.

51. Livak K J, Schmittgen T D (2001) Analysis of relative gene expression data using real-time quantitative PCR and the 2−ΔΔCT method. Methods 25(4):402-408.

52. Alhasan A H, et al. (2016) Circulating microRNA signature for the diagnosis of very high-risk prostate cancer. Proc Natl Acad Sci USA 113(38):10655-10660.

REFERENCES

Example 2

Bertoni-Freddari, C., Fattoretti, P., Casoli, T., Caselli, U., and Meier-Ruge, W. (1996). Deterioration threshold of synaptic morphology in aging and senile dementia of Alzheimer's type. Anal. Quant. Cytol. Histol. 18, 209-213.

Burton, T., Liang, B., Dibrov, A., and Amara, F. (2002). Transforming growth factor-beta-induced transcription of the Alzheimer beta-amyloid precursor protein gene involves interaction between the CTCFcomplex and Smads. Biochem. Biophys. Res. Commun. 295, 713-723. doi: 10.1016/50006-291X(02)00725-8

Chen, W., Chen, L., Zhang, Z., Meng, F., Huang, G., Sheng, P., et al. (2016). MicroRNA-455-3p modulates cartilage development and degeneration through modification of histone H3 acetylation. Biochim. Biophys. Acta 1863, 2881-2891. doi: 10.1016/j.bbamcr.2016.09.010

Cheng, C. M., Shiah, S. G., Huang, C. C., Hsiao, J. R., and Chang, J. Y. (2016). Upregulation of miR-455-5p by the TGF-b-SMAD signalling axis promotes the proliferation of oral squamous cancer cells by targeting UBE2B. J. Pathol. 240, 38-49. doi: 10.1002/path.4752

DeKosky, S. T., Scheff, S. W., and Styrene, S. D. (1996). Structural correlates of cognition in dementia: quantification and assessment of synapse change. Neurodegeneration 5, 417-421. doi: 10.1006/neur.1996.0056

De Rossi, P., Buggia-Prévot, V., Clayton, B. L., Vasquez, J. B., van Sanford, C., Andrew, R. J., et al. (2016). Predominant expression of Alzheimer's disease associated BIN1 in mature oligodendrocytes and localization to white matter tracts. Mol. Neurodegener. 11:59. doi: 10.1186/s13024-016-0124-1

Du, H., Guo, L., Yan, S., Sosunov, A. A., McKhann, G. M., and Yan, S. S. (2010). Early deficits in synaptic mitochondria in an Alzheimer's disease mouse model. Proc. Natl. Acad. Sci. U.S.A. 107, 18670-18675. doi: 10.1073/pnas.1006586107

Ferguson, S. A., Panos, J. J., Sloper, D., and Varma, V. (2017). Neurodegenerative markers are increased in postmortemBA21 tissue fromAfrican Americans with Alzheimer's disease. J. Alzheimers Dis. 59, 57-66. doi: 10.3233/JAD-170204

Hamam, R., Ali, A. M., Alsaleh, K. A., Kassem, M., Alfayez, M., Aldahmash, A., et al. (2016). microRNA expression profiling on individual breast cancer patients identifies novel panel of circulating microRNA for early detection. Sci. Rep. 6:25997. doi: 10.1038/srep25997

Jung, E. S., Choi, H., Song, H., Hwang, Y. J., Kim, A., Ryu, H., et al. (2016). p53-dependent SIRT6 expression protects Ab42-induced DNA damage. Sci. Rep. 6:25628. doi:10.1038/srep25628

Jung, E. S., Hong, H., Kim, C., and Mook-Jung, I. (2015). Acute ER stress regulates amyloid precursor protein processing through ubiquitin-dependent degradation. Sci. Rep. 5:8805. doi: 10.1038/srep08805

Khan, T. K., and Alkon, D. L. (2016). An internally controlled peripheral biomarker for Alzheimer's disease: Erk1 and Erk2 responses to the inflammatory signal bradykinin. Proc. Natl. Acad. Sci. U.S.A. 103, 13203-13207. doi: 10.1073/pnas.0605411103

Kumar, S., Chawla, Y. K., Ghosh, S., and Chakraborti, A. (2014). Severity of hepatitis C virus (genotype-3) infection positively correlates with circulating microRNA-122 in patients sera. Dis. Markers 2014:435476. doi: 10.1155/2014/435476

Kumar, S., and Reddy, P. H. (2016). Are circulating microRNAs peripheral biomarkers for Alzheimer's disease?. Biochim. Biophys. Acta 1862, 1617-1627. doi: 10.1016/j.bbadis.2016.06.001

Kumar, S., Vijayan, M., and Reddy, P. H. (2017). MicroRNA-455-3p as a potential peripheral biomarker for Alzheimer's disease. Hum. Mol. Genet. 26, 3808-3822. doi: 10.1093/hmg/ddx267

Kuruva, C. S., Manczak, M., Yin, X., Ogunmokun, G., Reddy, A. P., and Reddy, P. H. (2017). Aqua-soluble DDQ reduces the levels of Drp1 and Ab and inhibits abnormal interactions between Ab and Drp1 and protects Alzheimer's disease neurons from Ab- and Drp1-induced mitochondrial and synaptic toxicities. Hum. Mol. Genet. 26, 3375-3395. doi: 10.1093/hmg/ddx226

LaFerla, F. M., Green, K. N., and Oddo, S. (2007). Intracellular amyloid-beta in Alzheimer's disease. Nat. Rev. Neurosci. 8, 499-509. doi: 10.1038/nrn2168

Li, Q., Athan, E. S., Wei, M., Yuan, E., Rice, S. L., Vonsattel, J. P., et al. (2004). TP73 allelic expression in human brain and allele frequencies in Alzheimer's disease. BMC Med. Genet. 5:14. doi: 10.1186/1471-2350-5-14

Li, Y. J., Ping, C., Tang, J., and Zhang, W. (2016). MicroRNA-455 suppresses non-small cell lung cancer through targeting ZEB1. Cell Biol. Int. 40, 621-628. doi: 10.1002/cbin.10584

Liu, J., Zhang, J., Li, Y., Wang, L., Sui, B., and Dai, D. (2016). MiR-455-5p acts as a novel tumor suppressor in gastric cancer by down-regulating RAB18. Gene 592, 308-315. doi: 10.1016/j.gene.2016.07.034

Malkki, H. (2015). Alzheimer disease: NGF gene therapy activates neurons in the AD patient brain. Nat. Rev. Neurol. 11:548. doi: 10.1038/nrneurol.2015.170

Mattson, M. P. (2004). Pathways towards and away from Alzheimer's disease. Nature 430, 631-639. doi: 10.1038/nature02621

McGeer, P. L., and McGeer, E. G. (1995). The inflammatory response system of brain: implications for therapy of Alzheimer and other neurodegenerative diseases. Brain Res. Rev. 21, 195-218. doi: 10.1016/0165-0173(95)00011-9

Nunomura, A., Perry, G., Aliev, G., Hirai, K., Takeda, A., Balraj, E. K., et al. (2001). Oxidative damage is the earliest event in Alzheimer disease. J. Neuropathol. Exp. Neurol. 60, 759-767. doi: 10.1093/jnen/60.8.759

Qin, L., Zhang, Y., Lin, J., Shentu, Y., and Xie, X. (2016). MicroRNA-455 regulates migration and invasion of human hepatocellular carcinoma by targeting Runx2. Oncol. Rep. 36, 3325-3332. doi: 10.3892/or.2016.5139

Reddy, P. H. (2006). Amyloid precursor protein-mediated free radicals and oxidative damage: implications for the development and progression of Alzheimer's disease. J. Neurochem. 96, 1-13. doi: 10.1111/j.1471-4159.2005.03530.x Reddy, P. H., and Beal, M. F. (2008). Amyloid beta, mitochondrial dysfunction and synaptic damage: implications for cognitive decline in aging and Alzheimer's disease. Trends Mol. Med. 14, 45-53. doi: 10.1016/j.molmed.2007.12.002

Reddy, P. H., Manczak, M., Mao, P., Calkins, M. J., Reddy, A. P., and Shirendeb, U. (2010). Amyloid-beta and mitochondria in aging and Alzheimer's disease: implications for synaptic damage and cognitive decline. J. Alzheimers Dis. 20, S499-S512. doi: 10.3233/JAD-2010-100504

Reddy, P. H., Tonk, S., Kumar, S., Vijayan, M., Kandimalla, R., Kuruva, C. S., et al. (2017). A critical evaluation of neuroprotective and neurodegenerative MicroRNAs in Alzheimer's disease. Biochem. Biophys. Res. Commun. 483, 1156-1165. doi: 10.1016/j.bbrc.2016.08.067

Reddy, P. H., Tripathi, R., Troung, Q., Tirumala, K., Reddy, T. P., Anekonda, V., et al. (2012). Abnormal mitochondrial dynamics and synaptic degeneration as early events in Alzheimer's disease: implications to mitochondria targeted antioxidant therapeutics. Biochim. Biophys. Acta 1822, 639-649. doi: 10.1016/j.bbadis.2011.10.011

Shackleton, B., Crawford, F., and Bachmeier, C. (2017). Apolipoprotein E mediated modulation of ADAM10 in Alzheimer's disease. Curr. Alzheimer Res. 14, 578-585. doi: 10.2174/1567205014666170203093219

Sindi, I. A., Tannenberg, R. K., and Dodd, P. R. (2014). Role for the neurexinneuroligin complex in Alzheimer's disease. Neurobiol. Aging 35, 746-756. doi: 10.1016/j.neurobiolaging.2013.09.032

Slifer, M. A., Martin, E. R., Bronson, P. G., Browning-Large, C., Doraiswamy, P. M., Welsh-Bohmer, K. A., et al. (2006). Lack of association between UBQLN1 and Alzheimer disease. Am. J. Med. Genet. B Neuropsychiatr. Genet. 141B, 208-213. doi: 10.1002/ajmg.b.30298

Swerdlow, R. H. (2011). Brain aging, Alzheimer's disease, and mitochondria. Biochim. Biophys. Acta 1812, 1630-1639. doi: 10.1016/j.bbadis.2011. 08.012

Tampellini, D., and Gouras, G. K. (2010). Synapses, synaptic activity and intraneuronal abeta in Alzheimer's disease. Front. Aging Neurosci. 2:13. doi: 10.3389/fnagi.2010.00013

Terry, R. D., Masliah, E., Salmon, D. P., Butters, N., DeTeresa, R., Hill, R., et al. (1991). Physical basis of cognitive alterations in Alzheimer's disease: synapse loss is the major correlate of cognitive impairment. Ann. Neurol. 30, 572-580. doi: 10.1002/ana.410300410

Toth, M. E., Szegedi, V., Varga, E., Juhász, G., Horvath, J., Borbély, E., et al. (2013). verexpression of Hsp27 ameliorates symptoms of Alzheimer's disease in APP/PS1 mice. Cell Stress Chaperones 18, 759-771. doi: 10.1007/s12192-013-0428-9

Vallortigara, J., Whitfield, D., Quelch, W., Alghamdi, A., Howlett, D., Hortobágyi, T., et al. (2016). Decreased levels of VAMP2 and monomeric alphasynuclein correlate with duration of dementia. J. Alzheimers Dis. 50, 101-110. doi: 10.3233/JAD-150707

Wilcock, D. M., Hurban, J., Helman, A. M., Sudduth, T. L., McCarty, K. L., Beckett, T. L., et al. (2015). Down syndrome individuals with Alzheimer's disease have a distinct neuroinflammatory phenotype compared to sporadic Alzheimer's disease. Neurobiol. Aging 36, 2468-2474. doi: 10.1016/j.neurobiolaging.2015.05.016

Williams, J., Smith, F., Kumar, S., Vijayan, M., and Reddy, P. H. (2016). Are microRNAs true sensors of ageing and cellular senescence?. Ageing Res. Rev. 35, 350-363. doi: 10.1016/j.arr.2016.11.008

World Alzheimer Report (2015). Publication Alzheimer's Association. Zhao, Y., Yan, M., Yun, Y., Zhang, J., Zhang, R., Li, Y., et al. (2017). MicroRNA-455-3p functions as a tumor suppressor by targeting eIF4E in prostate cancer. Oncol. Rep. 37, 2449-2458. doi: 10.3892/or.2017.5502

Zheng, J., Lin, Z., Zhang, L., and Chen, H. (2016). MicroRNA-455-3p inhibits tumor cell proliferation and induces apoptosis in HCT116 human colon cancer cells. Med. Sci. Monit. 18, 4431-4437. doi: 10.12659/MSM.898452

Zhu, X., Perry, G., Smith, M. A., and Wang, X. (2013). Abnormal mitochondrial dynamics in the pathogenesis of Alzheimer's disease. J. Alzheimers Dis. 33, S253-S262. doi: 10.3233/JAD-2012-129005

What is claimed is:

1. A method for identifying and treating an Alzheimer's Disease (AD) patient comprising:
   obtaining a blood, serum, or plasma sample from the AD patient;
   assessing the dataset for a presence or an increase in an amount of miRNA-455-3p;
   determining the deregulation of miR-455-3p by detecting the increase in miRNA-455-3p when compared to a healthy control to produce a score that is indicative of AD, wherein a higher score relative to a healthy control indicates that the patient has AD, wherein the healthy control is derived from a non-AD patient with no clinical evidence of AD;
   determining that the patient has AD, and
   based on the detection of the increase in miR-455-3p, administering a treatment to the AD patient a cyclooxygenase inhibitor, a Catecholamine transferase inhibitor, a protein kinases inhibitor, a Neurotransmitter transporter inhibitor, a Renin-angiotensin system inhibitor, or a HMG-CoA reductase inhibitor.

2. The method of claim 1, wherein the step of assessing comprises RT-PCR, qRT-PCR, biochip, singleplexed or multiplexed RT-PCR.

3. The method of claim 1, wherein obtaining the dataset associated with the sample comprises obtaining the sample and processing the sample to experimentally determine the dataset, or wherein obtaining the dataset associated with the sample comprises receiving the dataset from a third party that has processed the sample to experimentally determine the dataset.

4. The method of claim 1, wherein the healthy control is a pre-determined average level derived from a healthy individual with no clinically documented evidence of AD.

* * * * *

SEQUENCE LISTING

```
<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Synthetic primer

<400> SEQUENCE: 1
gcagtccatg ggcatataca c                                      21

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
```

```
gcagtccacg ggcatataca c                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic primer

<400> SEQUENCE: 3
ctgggctcgg gacgcgcggc t                                              21

<210> SEQ ID NO 4
<211> LENGTH: 23
<212> TYPE: DNA
<213> ORGANISM: Artificial Sequence
<220> FEATURE:
<223> OTHER INFORMATION: Synthetic primer

<400> SEQUENCE: 4
agggaaaaaa aaaaggattt gtc                                            23

<210> SEQ ID NO 5
<211> LENGTH: 24
<212> TYPE: DNA
<213> ORGANISM: Artificial Sequence
<220> FEATURE:
<223> OTHER INFORMATION: Synthetic primer

<400> SEQUENCE: 5
acaaaaaaaa aagcccaacc cttc                                           24

<210> SEQ ID NO 6
<211> LENGTH: 22
<212> TYPE: DNA
<213> ORGANISM: Artificial Sequence
<220> FEATURE:
<223> OTHER INFORMATION: Synthetic primer

<400> SEQUENCE: 6
ggcctcaggc aggcgcaccc ga                                             22

<210> SEQ ID NO 7
<211> LENGTH: 22
<212> TYPE: DNA
<213> ORGANISM: Artificial Sequence
<220> FEATURE:
<223> OTHER INFORMATION: Synthetic primer

<400> SEQUENCE: 7
gggtgggcca ggctgtgggg cg                                             22

<210> SEQ ID NO 8
<211> LENGTH: 23
<212> TYPE: DNA
<213> ORGANISM: Artificial Sequence
<220> FEATURE:
<223> OTHER INFORMATION: Synthetic primer

<400> SEQUENCE: 8
cgcttcggca gcacatatac taa                                            23

<210> SEQ ID NO 9
<211> LENGTH: 23
<212> TYPE: DNA
<213> ORGANISM: Artificial Sequence
```

```
<220> FEATURE:
<223> OTHER INFORMATION: Synthetic primer

<400> SEQUENCE: 9
tatggaacgc ttcacgaatt tgc                                            23

<210> SEQ ID NO 10
<211> LENGTH: 22
<212> TYPE: DNA
<213> ORGANISM: Artificial Sequence
<220> FEATURE:
<223> OTHER INFORMATION: Synthetic primer

<400> SEQUENCE: 10
agtacttttg aaccctttc ca                                              22
```